(12) United States Patent
Scutti et al.

(10) Patent No.: US 11,406,487 B2
(45) Date of Patent: *Aug. 9, 2022

(54) GRAFT WITH EXPANDABLE REGION AND METHODS OF MAKING AND USING THE SAME

(71) Applicant: ATRIUM MEDICAL CORPORATION, Merrimack, NH (US)

(72) Inventors: James J. Scutti, Arlington, MA (US); David G. Culp, Waxhaw, NC (US); Ibrahim E. Dagher, Pelham, NH (US); Kevin W. Penn, Nashua, NH (US)

(73) Assignee: ATRIUM MEDICAL CORPORATION, Merrimack, NH (US)

( * ) Notice: Subject to any disclaimer, the term of this patent is extended or adjusted under 35 U.S.C. 154(b) by 354 days.

This patent is subject to a terminal disclaimer.

(21) Appl. No.: 16/284,919

(22) Filed: Feb. 25, 2019

(65) Prior Publication Data

US 2019/0183631 A1   Jun. 20, 2019

Related U.S. Application Data

(62) Division of application No. 14/906,853, filed as application No. PCT/US2014/047711 on Jul. 22, 2014, now Pat. No. 10,245,137.

(Continued)

(51) Int. Cl.
*A61F 2/07*    (2013.01)
*A61F 2/915*    (2013.01)
(Continued)

(52) U.S. Cl.
CPC ............ *A61F 2/07* (2013.01); *A61F 2/915* (2013.01); *A61B 17/11* (2013.01); *A61B 2017/1107* (2013.01); *A61B 2017/1135* (2013.01); *A61B 2017/1139* (2013.01); *A61F 2/954* (2013.01); *A61F 2002/061* (2013.01);
(Continued)

(58) Field of Classification Search
CPC ......... A61F 2/04–2002/077; A61F 2/24–2424; A61F 2/82–945; A61F 2250/0039; A61F 2250/0012; A61F 2250/0048
See application file for complete search history.

(56) References Cited

U.S. PATENT DOCUMENTS 5,693,088 A    2/1997   Lazarus
5,676,697 A    10/1997  McDonald
(Continued)

FOREIGN PATENT DOCUMENTS

CN    1882293 A    12/2006
CN    201617973 U    11/2010
(Continued)

OTHER PUBLICATIONS

Examination Report issued in AU Application No. 2019204766 dated Jun. 5, 2020, 4 pages.
(Continued)

*Primary Examiner* — Rebecca S Preston

(57) ABSTRACT

A vascular graft suitable for implantation, and more particular to a vascular graft having an expandable outflow region for restoring patency of the graft after implantation into a body lumen.

13 Claims, 22 Drawing Sheets

Related U.S. Application Data

(60) Provisional application No. 61/857,181, filed on Jul. 22, 2013.

(51) Int. Cl.
*A61B 17/11* (2006.01)
*A61F 2/954* (2013.01)
*A61F 2/06* (2013.01)
*A61F 2/82* (2013.01)

(52) U.S. Cl.
CPC ... *A61F 2002/065* (2013.01); *A61F 2002/072* (2013.01); *A61F 2002/826* (2013.01); *A61F 2002/91575* (2013.01); *A61F 2002/91583* (2013.01); *A61F 2250/0018* (2013.01); *A61F 2250/0039* (2013.01); *A61F 2250/0048* (2013.01); *A61F 2250/0071* (2013.01)

(56) References Cited

U.S. PATENT DOCUMENTS

| 10,245,137 | B2* | 4/2019 | Scutti | A61F 2/07 |
|---|---|---|---|---|
| 2001/0039446 | A1 | 11/2001 | Edwin et al. | |
| 2001/0053929 | A1 | 12/2001 | Vonesh | A61F 2/07 623/1.12 |
| 2002/0052640 | A1 | 5/2002 | Bigus | A61F 2/07 623/1.11 |
| 2004/0034406 | A1 | 2/2004 | Thramann | |
| 2010/0145434 | A1 | 6/2010 | Thornton et al. | |
| 2012/0203264 | A1 | 8/2012 | Karwa et al. | |
| 2012/0323303 | A1 | 12/2012 | Ivancev | |
| 2013/0131780 | A1 | 5/2013 | Armstrong et al. | |

FOREIGN PATENT DOCUMENTS

| EP | 0696447 B1 | 1/2000 |
|---|---|---|
| EP | 1637090 A2 | 3/2006 |
| EP | 1666003 A1 | 6/2006 |
| JP | 8173548 A | 7/1996 |
| JP | 2002501779 A | 1/2002 |
| JP | 2002531219 A | 9/2002 |
| JP | 2006158968 A | 6/2006 |
| JP | 2006297128 A | 11/2006 |
| WO | 9712562 A1 | 4/1997 |
| WO | 9938455 A1 | 8/1999 |
| WO | 0033770 A2 | 6/2000 |
| WO | 2005023149 A2 | 3/2005 |

OTHER PUBLICATIONS

Office Action issued in EP Application No. 14830021.3 dated Nov. 30, 2020, 4 pages.
Office Action issued in U.S. Appl. No. 14/906,853 dated Jul. 25, 2017, 21 pages.
Restriction Requirement issued in U.S. Appl. No. 14/906,853 dated Feb. 17, 2017, 10 pages.
Canadian Office Action dated Nov. 2, 2018 for corresponding Canadian Patent Application No. 2,918,936, 5 pages.
Australian Office Action dated Dec. 19, 2018 for corresponding Australian Patent Application No. 2014293273, 4 pages.
Final Office Action issued in counterpart JP Application No. 2016-529844, dated Sep. 18, 2018.
Office Action issued in counterpart CN Application No. 201480049354.3, dated Dec. 9, 2016.
Office Action issued in counterpart CN Application No. 201480049354.3, dated Sep. 27, 2017.
Official Action issued in counterpart JP Application No. 2016-529844, dated Feb. 3, 2017.
Official Action issued in counterpart JP Application No. 2016-529844, dated Oct. 18, 2017.
Examination Report issued in counterpart EP Application No. 14830021.3, dated Aug. 1, 2018.
Examination Report issued in counterpart AU Application No. 2014293273, dated Apr. 12, 2018.
International Preliminary Report on Patentability issued in counterpart PCT Application No. PCT/US2014/047711, dated Jan. 26, 2016.
Examiner's Report issued for counterpart Canadian Application No. 2,918,936, dated Mar. 8, 2018.
Extended European Search Report dated Nov. 23, 2016 issued for corresponding EP patent application No. 14830021.3, 8 pages.
International Search Report dated Jan. 12, 2015 issued for corresponding international application No. PCT/US2014/047711, 4 pages.
Pre-Appeal Examination Report issued in counterpart JP Application No. 2016-529844, dated Apr. 23, 2019.
Office Action issued in counterpart CN Application No. 201810356706.X, dated Nov. 25, 2019.
Official Action dated Jan. 5, 2021 in Japanese Application No. 2019-169175, 4 pages.

* cited by examiner

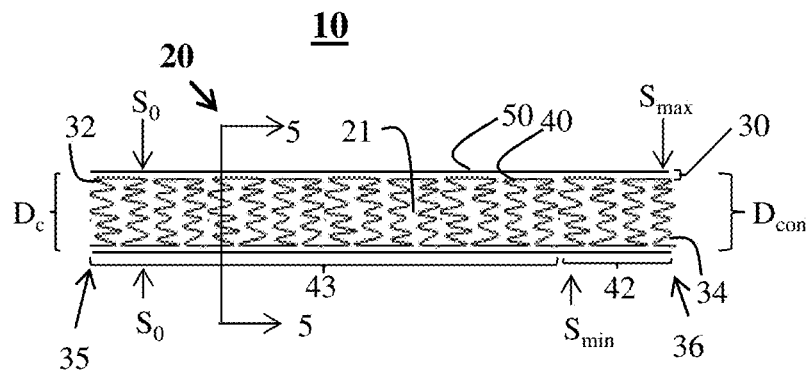
FIG. 1A
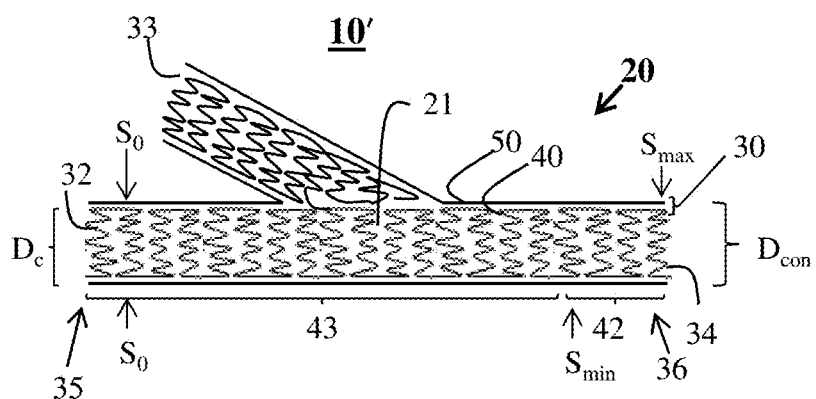
FIG. 1B
FIGS. 1A-1B

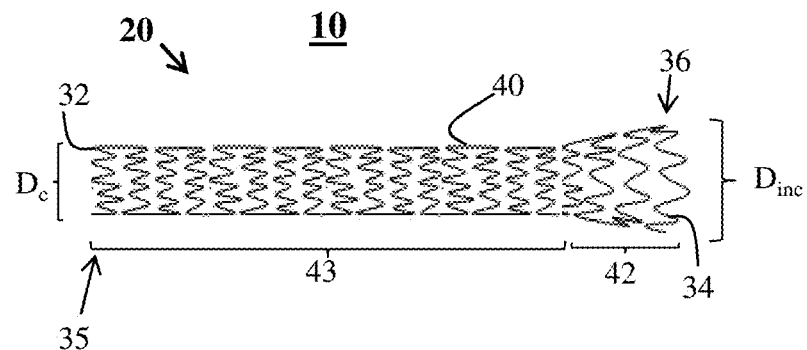
*FIG. 2A*
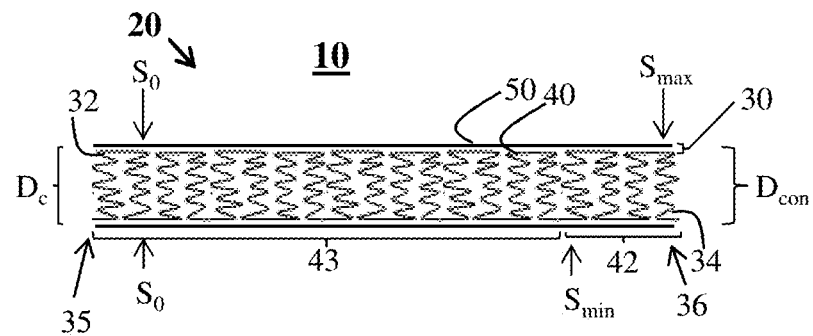
*FIG. 2B*
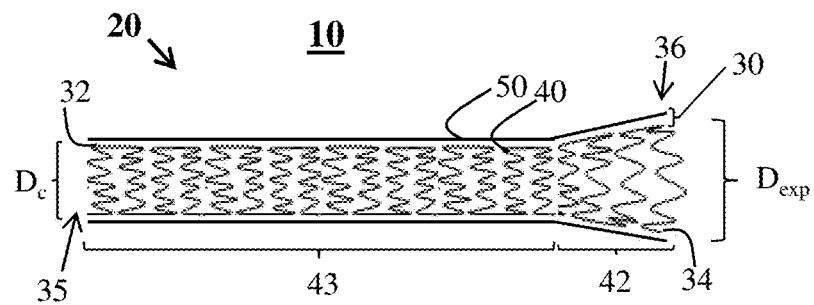
*FIG. 2C*
FIGS. 2A-2C

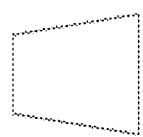
FIG. 3A
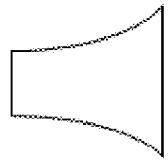
FIG. 3F
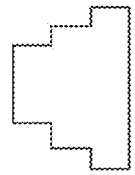
FIG. 3K
FIG. 3B
FIG. 3G
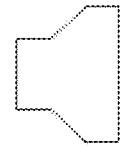
FIG. 3L
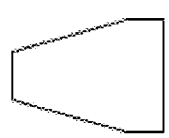
FIG. 3C
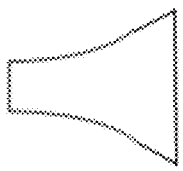
FIG. 3H
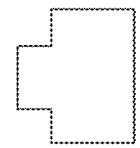
FIG. 3M
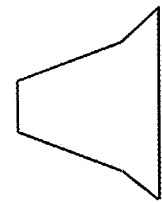
FIG. 3D
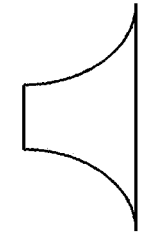
FIG. 3I
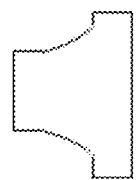
FIG. 3N
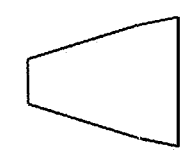
FIG. 3E
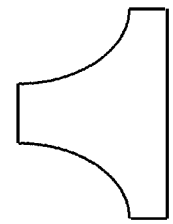
FIG. 3J
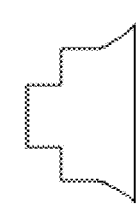
FIG. 3O
FIGS. 3A-3O

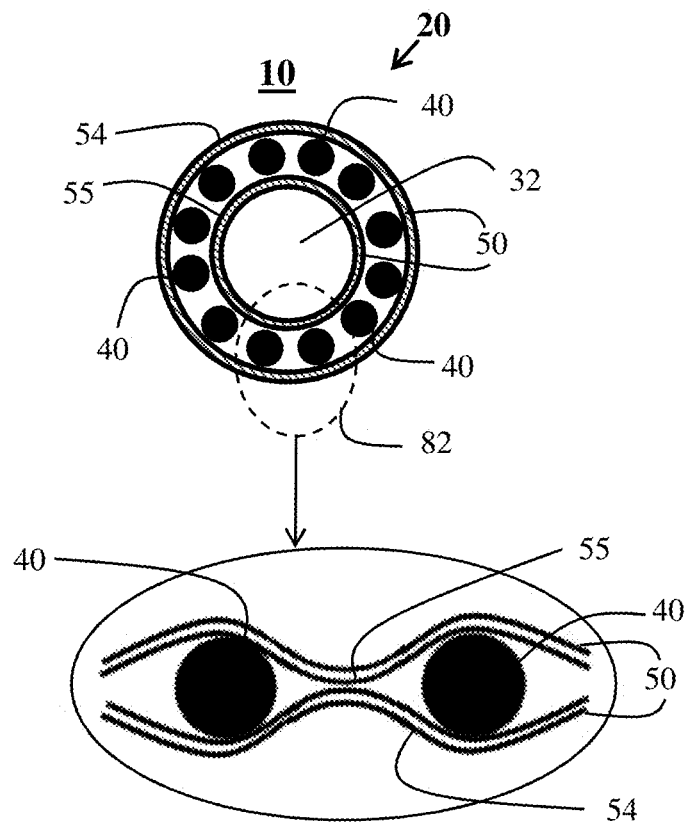
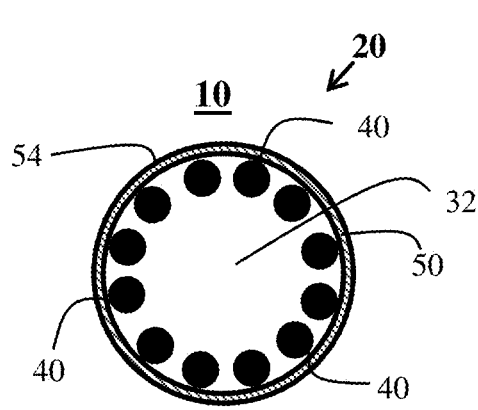
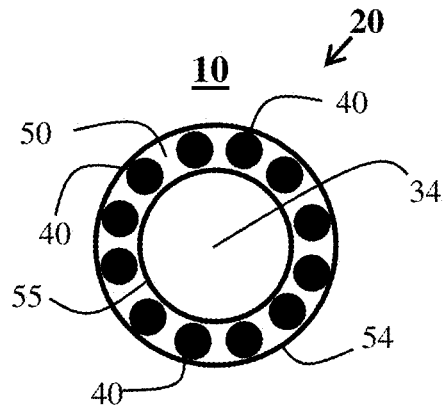
FIGS. 5A-5D

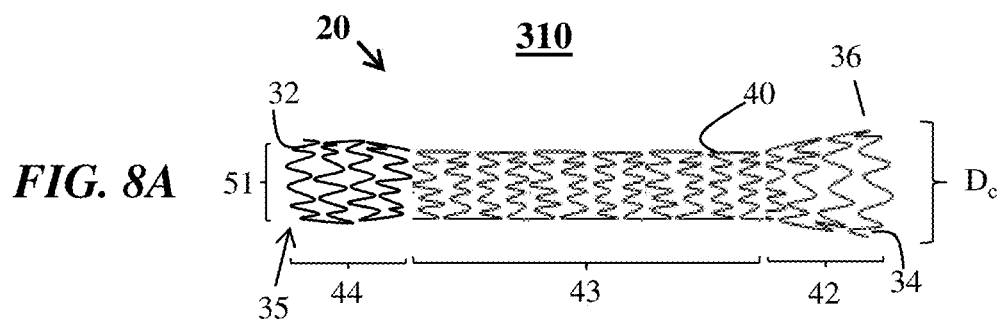
*FIG. 8A*
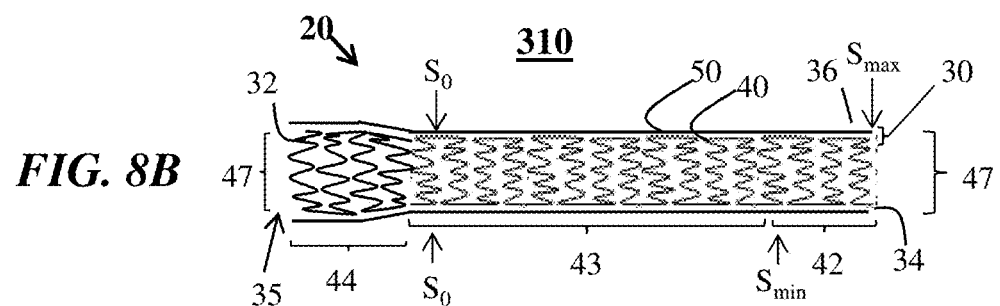
*FIG. 8B*
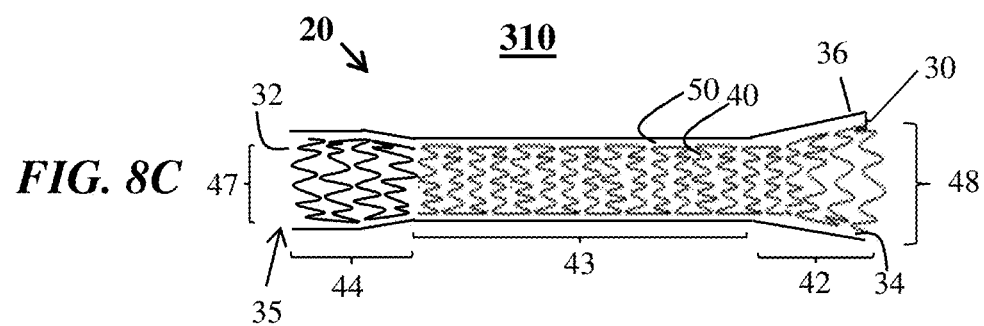
*FIG. 8C*
*FIGS. 8A-8C*

*FIG. 9D*
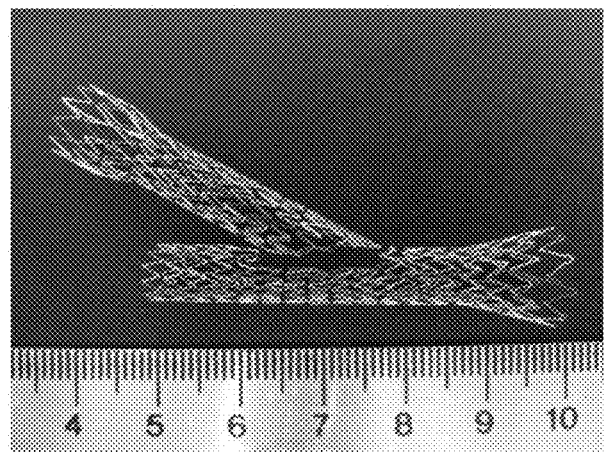
*FIG. 9E*
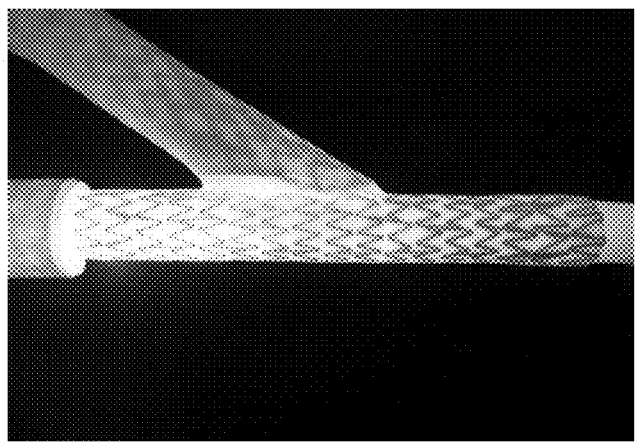
*FIG. 9F*
*FIGS. 9D-9F*

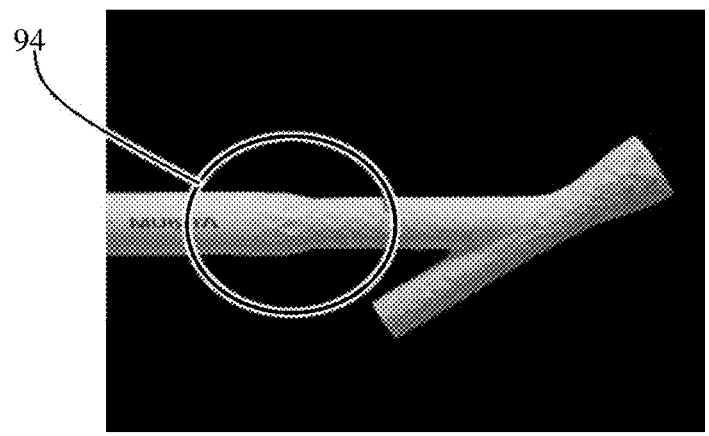
FIG. 9G
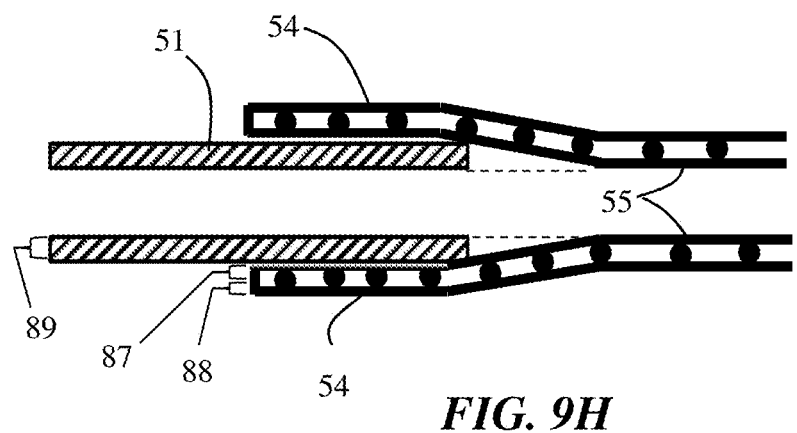
FIG. 9H
FIGS. 9G-9H

*FIG. 14A*
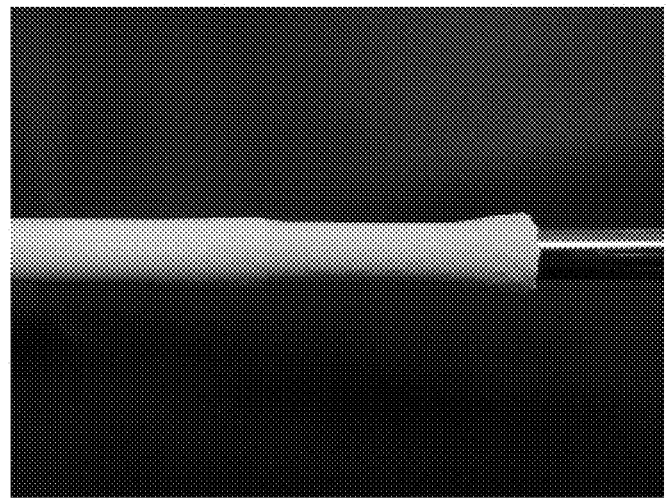
*FIG. 14B*
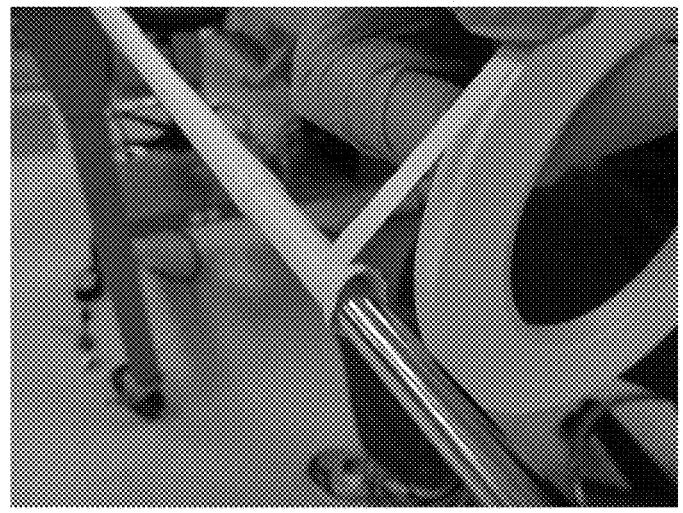
*FIGS. 14A-14B*

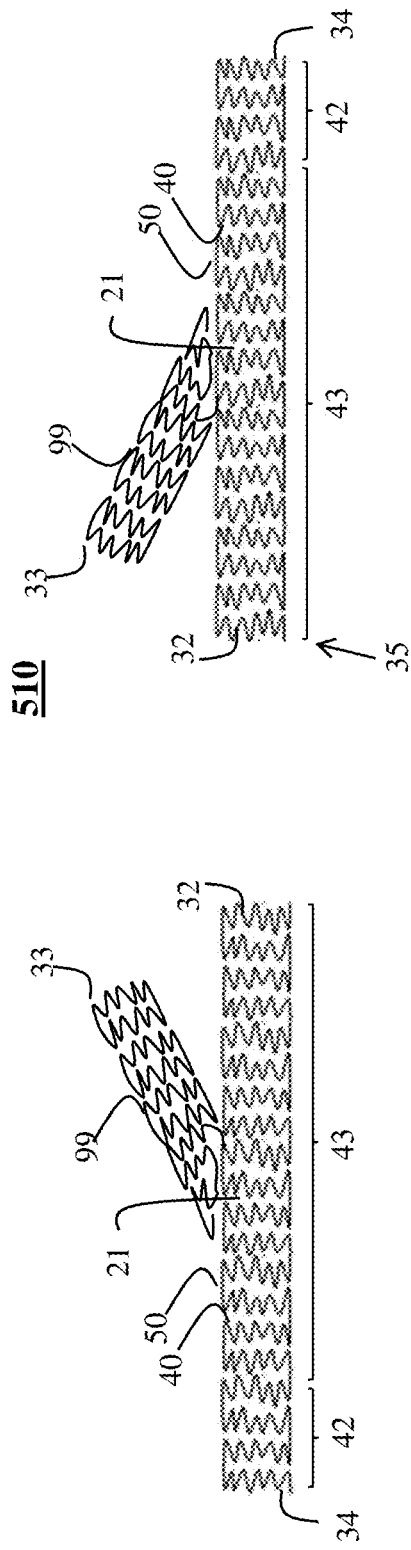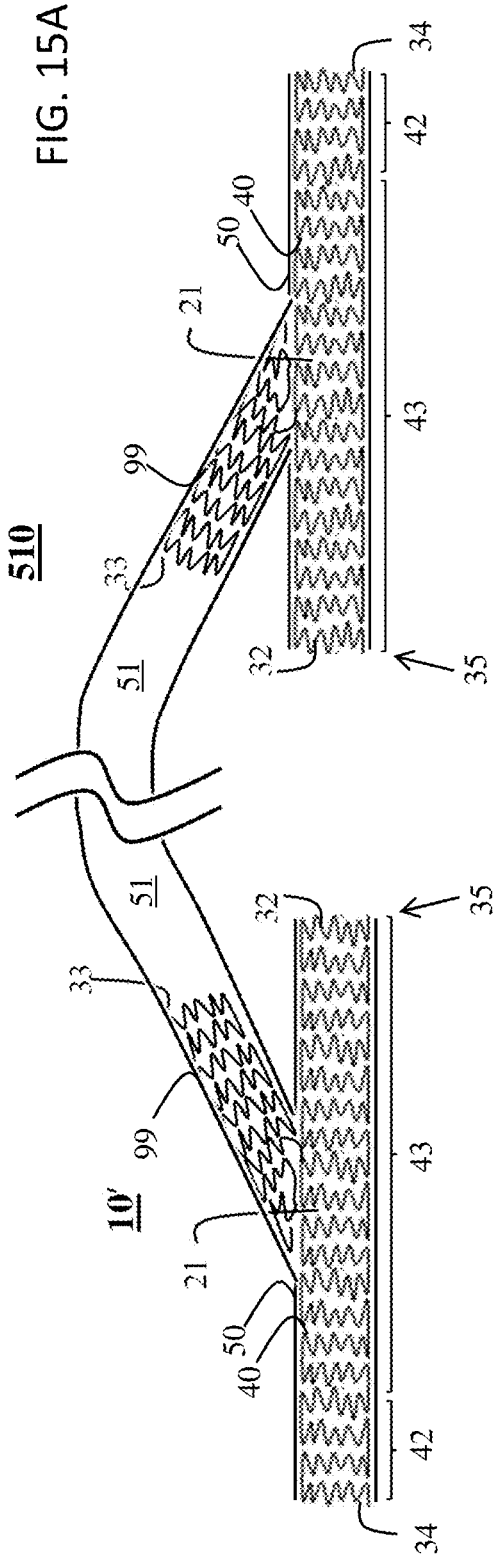

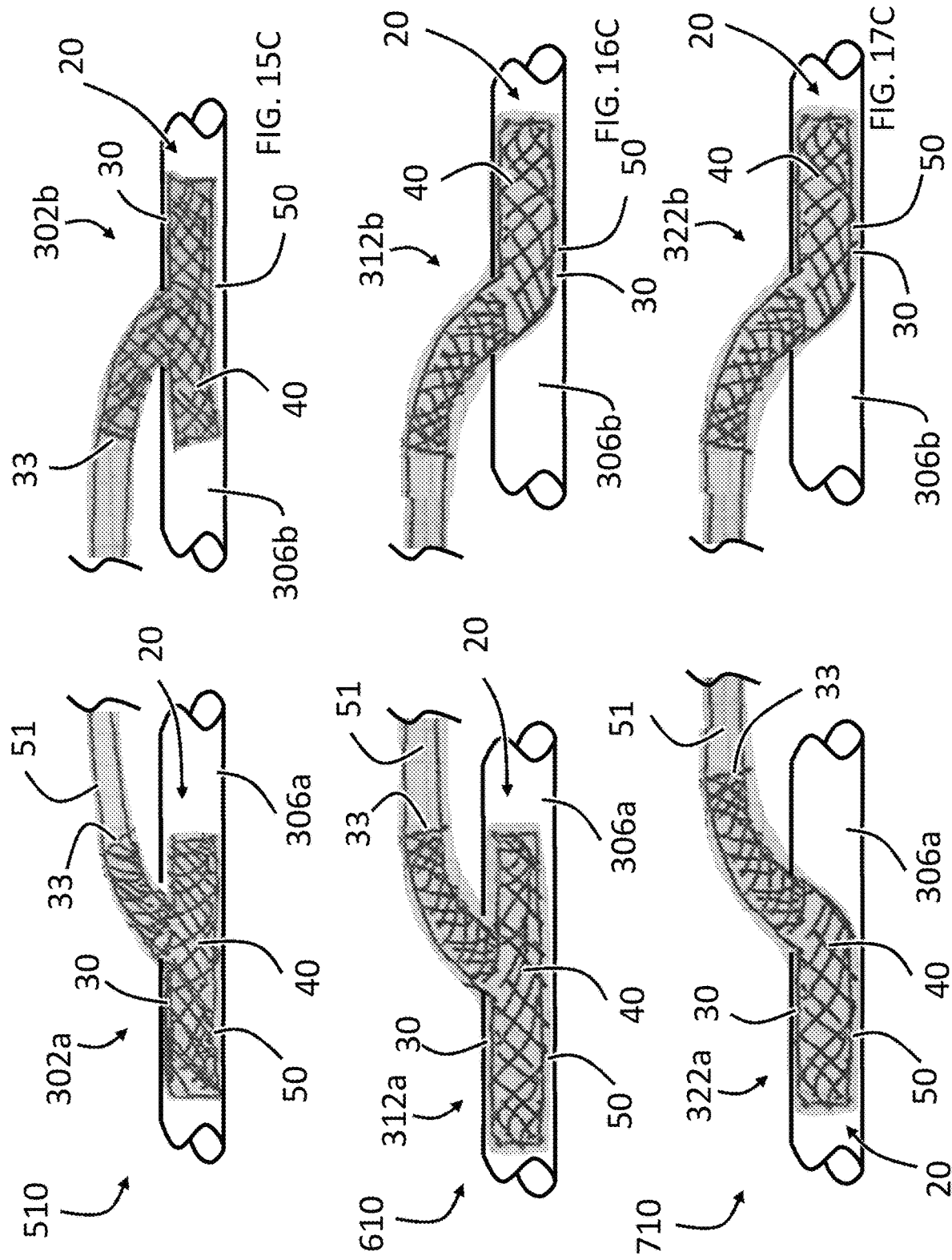

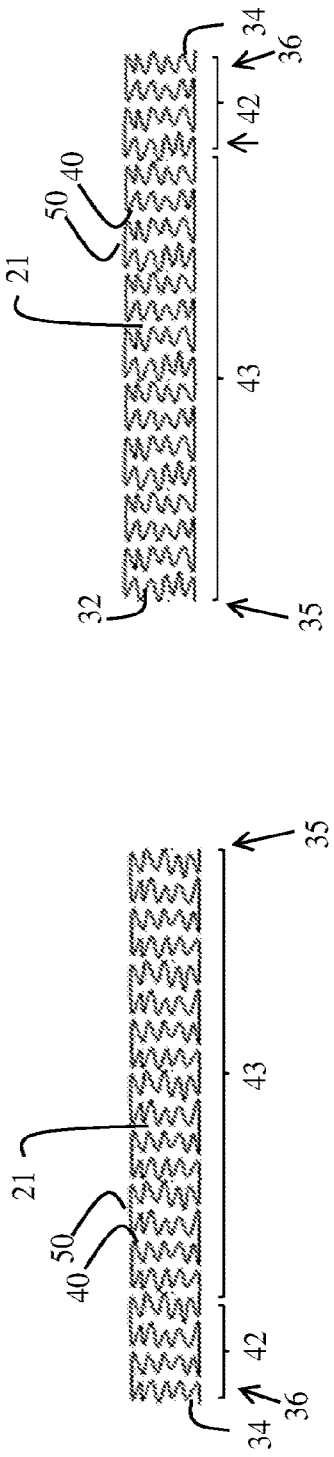
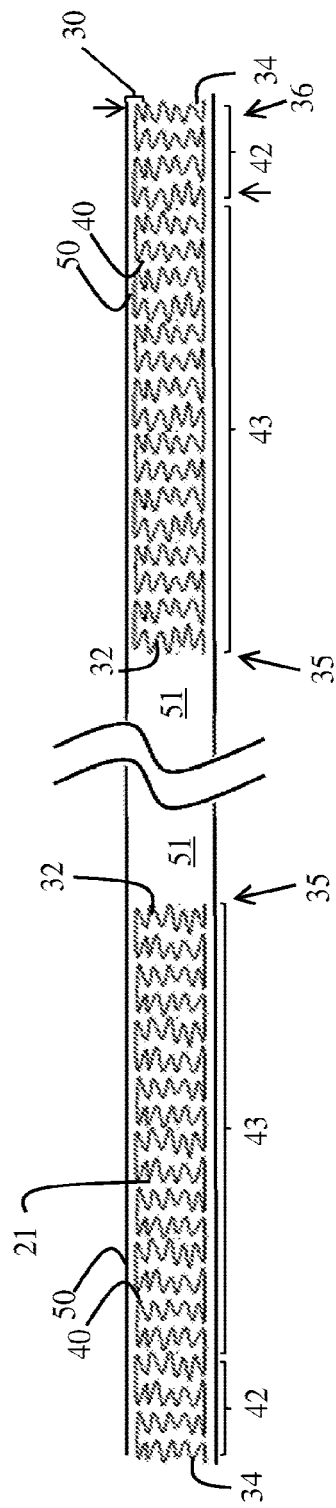
FIG. 17A
FIG. 17B

GRAFT WITH EXPANDABLE REGION AND METHODS OF MAKING AND USING THE SAME

CROSS-REFERENCE TO RELATED APPLICATIONS

This application is a divisional of U.S. application Ser. No. 14/906,853, filed Jan. 21, 2016, which is a national stage application of International Application No. PCT/US2014/047711, filed Jul. 22, 2014, which claims the benefit of priority to U.S. Provisional Patent Application No. 61/857,181, filed Jul. 22, 2013. The contents of U.S. application Ser. No. 14/906,853 (filed Jan. 21, 2016), International Application No. PCT/US2014/047711 (filed Jul. 22, 2014), and U.S. Provisional Patent Application No. 61/857,181 (filed Jul. 22, 2013) which are each incorporated herein by reference in their entireties entirety.

FIELD OF THE INVENTION

The present invention and disclosure relates to various embodiments of vascular grafts suitable for implantation, including the manufacturing and use of such grafts. In certain embodiments of the present disclosure, one or more expandable first regions are provided for restoring patency of the graft after implantation into a body lumen.

BACKGROUND OF THE INVENTION

Vascular diseases are prevalent worldwide. Bypass surgery, whereby a conduit, either artificial or autologous, is grafted into an existing vessel to circumvent a diseased portion of the vessel or to restore blood flow around a blocked or damaged blood vessel, is one of the most common treatments for such diseases.

Vascular grafts are also used as entry sites in dialysis patients. The graft connects or bridges an artery to a vein in the patient's body. A needle is inserted into the graft, allowing for blood to be withdrawn and passed through a hemodialysis machine and returned to the patient through a second needle inserted into the graft.

A significant number of by-pass grafts fail within 5 to 7 years. The average life-span for hemodialysis grafts is even shorter, often less than two years. A primary cause of graft failure is the closing of the graft due to tissue in-growth and eventually thrombosis formation. The smaller the graft diameter, the higher the graft failure rate. The lost patency resulting from graft closure or collapse is particularly problematic at the outflow site where the outflow end of the graft touches the vessel.

However, this issue has not been adequately addressed by conventional techniques to restore patency, which typically include surgical procedures (e.g., thrombectomy or percutaneous thrombectomy) or chemical intervention techniques (e.g., administration of anti-clotting or anti-platelet drugs, such as ticlopidine, aspirin, dipyridimole, or clopidogrel) to remove ingrown tissue or clotting that otherwise contributes to graft failure. In particular, surgical and chemical interventions can introduce unnecessary risk (e.g., of infection, bleeding, etc.) and often are inadequately effective to maintain patency over longer periods of time.

Thus, there is a need for a graft for which patency can be restored easily after implantation without requiring risky and ineffective chemical or surgical interventions. There is also a need for different graft structures that utilize various features of the graft technologies disclosed herein.

SUMMARY

There is a need for a vascular graft having an expandable outflow region which enables patency to be restored easily after implantation without requiring risky and ineffective chemical or surgical interventions. Embodiments of the present disclosure and invention are directed toward further solutions to address the aforementioned needs, in addition to having other desirable characteristics.

In accordance with an embodiment of the present invention, a graft is provided. The graft includes a conduit having a wall. The conduit includes at least one inflow aperture at an inflow end of a body region, and an outflow aperture at an outflow end of an outflow region opposite from the at least one inflow aperture. The wall includes a support structure and a biocompatible layer. The support structure along the outflow region is under continuous compressive stress resulting from a continuous applied load caused by the biocompatible layer against the support structure.

In accordance with aspects of the present invention, the compressive stress resulting from the continuous applied load in the outflow region is greater than a compressive stress resulting from a continuous applied load in the body region. In accordance with aspects of the present invention, the compressive stress experienced by the support structure resulting from the continuous applied load in the outflow region is incrementally greater at each segment along the support structure that is incrementally more distal from the at least one inflow aperture. The compressive stress experienced by the support structure resulting from the continuous applied load in the outflow region causes an elastic deformation of the support structure in the outflow region. In accordance with aspects of the present invention, the elastic deformation of the support structure in the outflow region is incrementally greater at each segment along the support structure that is incrementally more distal from the at least one inflow aperture. The elastic deformation of the support structure in the outflow region is reversible. The compressive stress resulting from the continuous applied load in the body region does not elastically deform the support structure in the body region.

In accordance with aspects of the present invention, the support structure prior to combination with the biocompatible layer to form the wall has multiple effective outer diameter measurements, and the support structure after combination with the biocompatible layer to form the wall has a generally uniform effective outer diameter measurement. The multiple effective outer diameter measurement along the body region can be a constant effective outer diameter measurement. The multiple effective outer diameter measurement along the outflow region can be an effective outer diameter measurement that is incrementally greater at each segment along the support structure that is incrementally more distal from the at least one inflow aperture. The generally uniform effective outer diameter measurement can be a constant effective outer diameter measurement along the body region, and a constrained effective outer diameter measurement along the outflow region. The constrained effective outer diameter measurement is approximately equal to the constant effective outer diameter measurement. The compressive stress resulting from the continuous applied load maintains the support structure along the outflow region at the constrained effective outer diameter measurement.

In accordance with aspects of the present invention, a counter force comprising a radial expansion force applied to the support structure along the outflow region causes plastic deformation of the biocompatible layer. The counter force comprising a radial expansion force applied to the support structure in the outflow region causes a reduction of the compressive stress experienced by the support structure. Following application of a counter force comprising a radial expansion force applied to the support structure in the outflow region, the graft reconfigures in such a way as to result in a plastically deformed biocompatible layer and a compressive stress experienced by the support structure that is less than the compressive stress experienced by the support structure prior to application of the counter force. Following application of a counter force comprising a radial expansion force applied to the support structure in the outflow region, the graft reconfigures in such a way as to result in a plastically deformed biocompatible layer. Following application of a counter force comprising a radial expansion force applied to the support structure in the outflow region, the graft reconfigures in such a way as to result in the support structure experiencing residual compressive stress where there was previously continuous compressive stress experienced by the support structure prior to application of the counter force.

In accordance with aspects of the present invention, a counter force comprising a radial expansion force applied to the support structure in the outflow region reconfigures the support structure along the outflow region from the constrained effective outer diameter measurement to an expanded effective outer diameter measurement that is greater than the constrained effective outer diameter measurement along at least a portion of the support structure in the outflow region. In accordance with aspects of the present invention, the expanded effective outer diameter measurement is at least 1 mm greater than the constrained effective outer diameter measurement along at least a portion of the support structure in the outflow region. In accordance with aspects of the present invention, the expanded effective outer diameter measurement of the support structure along the outflow region after being reconfigured is at least 1 mm greater than the constrained effective outer diameter measurement along the entire portion of the support structure in the outflow region.

In accordance with further aspects of the present invention, conduit can include a second inflow aperture. The longitudinal axis of the second inflow aperture intersects a longitudinal axis of the at least one inflow aperture at a non-parallel angle. In accordance with aspects of the present invention, the non-parallel angle comprises an angle between about 25° and 45°. In accordance with one aspect of the present invention, the non-parallel angle is about 35°.

In accordance with aspects of the present invention, the support structure is constructed of a shape memory alloy. In accordance with one aspect of the present invention, the support structure is constructed of nitinol. The support structure can have a zigzag wire shape.

In accordance with aspects of the present invention, the biocompatible layer comprises an expandable polymer. The biocompatible layer can include ePTFE. The biocompatible can include a biocompatible outer layer. The biocompatible layer can include a biocompatible inner layer. The biocompatible outer layer and the biocompatible inner layer encapsulate the support structure. In accordance with one aspect of the present invention, the biocompatible layer is not a surface modifying coating.

In accordance with one example embodiment, a vascular graft is provided. The vascular graft includes a conduit having a wall. The wall includes at least one inflow aperture at an inflow end of a body region, and an outflow aperture at an outflow end of an outflow region opposite from the at least one inflow aperture. The wall includes a support structure and a biocompatible layer. Prior to combination with the biocompatible layer to form the wall, the support structure includes multiple effective outer diameter measurements along its length. The multiple effective outer diameter measurements include a constant effective outer diameter measurement along the body region, and an effective outer diameter measurement along the outflow region that is incrementally greater at each segment along the support structure that is incrementally more distal from the at least one inflow aperture. After combination with the biocompatible layer to form the wall, the support structure in the outflow region is under continuous compressive stress resulting from a continuous applied load caused by the biocompatible layer which maintains the support structure along the outflow region at a constrained effective outer diameter measurement that is not incrementally greater at each segment along the support structure that is incrementally more distal from the at least one inflow aperture. After application of a counter force to the support structure in the outflow region the support structure in the outflow region is reconfigured from the constrained effective outer diameter measurement to an expanded effective outer diameter measurement, at least a portion of which is at least one millimeter greater than the constrained effective outer diameter measurement.

In accordance with an example embodiment of the present invention, a method of expanding an outflow end of an implanted graft is provided. The method includes (a) identifying an implanted graft and (b) and applying a counterforce. The vascular graft includes a conduit having a wall. The conduit includes at least one inflow aperture at an inflow end of a body region, and an outflow aperture at the outflow end of an outflow region opposite from the at least one inflow aperture. The wall includes a support structure and a biocompatible layer. Prior to combination with the biocompatible layer to form the wall, the support structure comprises multiple effective outer diameter measurements comprising a constant effective outer diameter measurement along the body region and an effective outer diameter measurement along the outflow region that is incrementally greater at each segment along the support structure that is incrementally more distal from the at least one inflow aperture. After combination with the biocompatible layer to form the wall, the support structure in the outflow region is under continuous compressive stress resulting from a continuous applied load caused by the biocompatible layer which maintains the support structure in the outflow region at a constrained effective outer diameter measurement that is not incrementally greater at each segment along the support structure that is incrementally more distal from the at least one inflow aperture. Application of the counter force to the support structure in the outflow region reconfigures the support structure along the outflow region from the constrained effective outer diameter measurement to an expanded effective outer diameter measurement that is greater than the constrained effective outer diameter measurement, thereby expanding the outflow region of the implanted graft.

In accordance with aspects of the present invention, the outflow region comprises an outflow end that has collapsed, stenosed, or has sustained intimal hyperplasia. The outflow end that has collapsed, stenosed, or has sustained intimal hyperplasia end impairs patency of a vessel in which the graft is implanted.

In accordance with aspects of the present invention, applying the counter force comprises expanding an expandable device in the outflow region of the implanted graft. Prior to expanding the expandable device the expandable device is advanced to the outflow region. Prior to advancing the expandable device to the outflow region, the expandable device is introduced into the implanted graft percutaneously.

In accordance with aspects of the present invention, the expanded effective outer diameter measurement is at least one millimeter greater than the constrained effective outer diameter measurement. In accordance with aspects of the present invention, the expanded effective outer diameter measurement is at least one millimeter greater than the constrained effective outer diameter measurement along any portion of the support structure in the outflow region.

In accordance with one example embodiment, a method of expanding an outflow region of an implanted graft is provided. The method includes (a) providing an implanted graft having an expandable outflow region, and (b) applying a counter force to the outflow region. The implanted graft includes a conduit having a wall. The conduit includes at least one inflow aperture at an inflow end of a body region, and an outflow aperture at the outflow end of an outflow region opposite from the at least one inflow aperture. The wall includes a support structure and a biocompatible layer. The support structure in the outflow region is under compressive stress resulting from an applied load caused by the biocompatible layer. Applying a counter force to the support structure in the outflow region reconfiguring the support structure along the outflow region from a constrained effective outer diameter measurement to an expanded effective outer diameter measurement that is greater than the constrained effective outer diameter measurement, thereby expanding the outflow end of the implanted graft.

In accordance with one example embodiment of the present invention, a method of making a graft having an expandable outflow end is provided. The method includes (a) providing a support structure having at least one inflow aperture at an inflow end of a body region and an outflow aperture at an outflow end of an outflow region opposite from the at least one inflow aperture. The support structure has multiple effective outer diameter measurements comprising a constant effective outer diameter measurement along the body region of the support structure and an incrementally increasing effective outer diameter measurement along the outflow region of the support structure. The method further includes (b) combining the support structure with at least one biocompatible layer to form a wall comprising the support structure and the at least one biocompatible layer. The method further includes (c) inserting a mandrel into the outflow aperture proximal to the outflow end of the support structure. The method further includes (d) constraining the incrementally increasing effective outer diameter measurement proximal to the outflow region of the support structure with a compression wrap in such a way that a continuous compressive stress results from a continuous applied load caused by the biocompatible layer which maintains the support structure along the outflow region in a constrained effective outer diameter measurement that is uniform with the constant effective outer diameter measurement. The method further includes (e) sintering the at least one biocompatible layer at a segment in the outflow region.

BRIEF DESCRIPTION OF THE FIGURES

These and other characteristics of the present invention will be more fully understood by reference to the following detailed description in conjunction with the attached drawings, in which:

FIG. 1A is a schematic view of a vascular graft according to an embodiment of the present invention;

FIG. 1B is a schematic view of a vascular graft according to another embodiment of the present invention;

FIG. 2A is a side view of an embodiment of a support structure of the vascular graft shown in FIG. 1A, illustrating the support structure prior to combination with a biocompatible layer, according to one aspect of the present invention;

FIG. 2B is a schematic view of an embodiment of the vascular graft shown in FIG. 1A after combining the support structure shown in FIG. 2A with the biocompatible layer, according to one aspect of the present invention;

FIG. 2C is a schematic view of an embodiment of the vascular graft shown in FIG. 1A after expanding the outflow region of the support structure of the vascular graft shown in FIG. 2B, according to one aspect of the present invention;

FIGS. 3A, 3B, 3C, 3D, 3E, 3F, 3G, 3H, 3I, 3J, 3K, 3L, 3M, 3N, and 3O are wireframe views showing various embodiments of the "flared" outflow region of the support structure, according to aspects of the present invention;

FIG. 5A is a cross-sectional view of a vascular graft similar to the one shown in FIG. 1A taken through sectional line 5-5 of FIG. 1A;

FIG. 5B is a detail view taken about the border 82 of FIG. 5A, according to one aspect of the present invention;

FIG. 5C is a cross-sectional view of a vascular graft similar to the one shown in FIG. 1A taken through sectional line 5-5 of FIG. 1A, according to one aspect of the present invention;

FIG. 5D is cross-sectional view of a vascular graft similar to the one shown in FIG. 1A taken through sectional line 5-5 of FIG. 1A, according to one aspect of the present invention;

FIG. 8A is a side view of an embodiment of a support structure similar to the vascular graft shown in FIG. 1A, illustrating the support structure prior to combination with the biocompatible layer, according to one aspect of the present invention;

FIG. 8B is a schematic view of an embodiment of the vascular graft shown in FIG. 8A after combining the support structure shown in FIG. 8A with the biocompatible layer, according to one aspect of the present invention;

FIG. 8C is a schematic view of an embodiment of the vascular graft shown in FIG. 8B after expanding the outflow region of the support structure shown in FIG. 8B, according to one aspect of the present invention;

FIG. 9D is a photograph of the embodiment of the support structure shown in FIG. 9A, according to one aspect of the present invention;

FIG. 9E is a photograph of the embodiment of the vascular graft shown in FIG. 9B, according to one aspect of the present invention;

FIG. 9F is a photograph of the embodiment of the vascular graft shown in FIG. 9C with an extension lumen extending from the branch, according to one aspect of the present invention;

FIG. 9G is a photograph similar to FIG. 9F further illustrating a border 84 encircling a portion of the graft at the branch, according to one aspect of the present invention;

FIG. 9H is a schematic representative detail cross-sectional view of an embodiment of FIGS. 9B and 9C taken about border 84 of FIG. 9G, according to an aspect of the present invention;

FIG. 14A is a photograph illustrating a step of a method of making a vascular graft according to one aspect of the present invention;

FIG. 14B is a photograph illustrating a step of a method of making a vascular graft according to one aspect of the present invention; and FIG. 15A is a schematic view of a vascular graft according to another embodiment of the present invention illustrating the support structure prior to combination with a biocompatible layer, according to one aspect of the present invention;

FIG. 15B is a schematic view of an embodiment of the support structure of FIG. 15A after the biocompatible layer(s) has been added to the support structure, according to one aspect of the present invention;

FIG. 15C is a schematic view of an embodiment of the vascular graft of FIG. 15B implanted into one or more vessels, according to one aspect of the present invention;

FIG. 16C is a schematic view of an embodiment of the vascular graft of FIG. 16B implanted into one or more vessels, according to one aspect of the present invention;

FIG. 17A is a schematic view of a vascular graft according to another embodiment of the present invention illustrating the support structure prior to combination with a biocompatible layer, according to one aspect of the present invention;

FIG. 17B is a schematic view of an embodiment of the support structure of FIG. 17A after the biocompatible layer(s) has been added to the support structure, according to one aspect of the present invention; and FIG. 17C is a schematic view of an embodiment of the vascular graft of FIG. 17B implanted into one or more vessels, according to one aspect of the present invention.

DETAILED DESCRIPTION

Figure 4A:
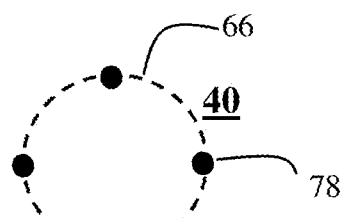
FIG. 4A is a schematic cross-sectional view of a support structure taken through line 68 of FIG. 4B.
Figure 4B:
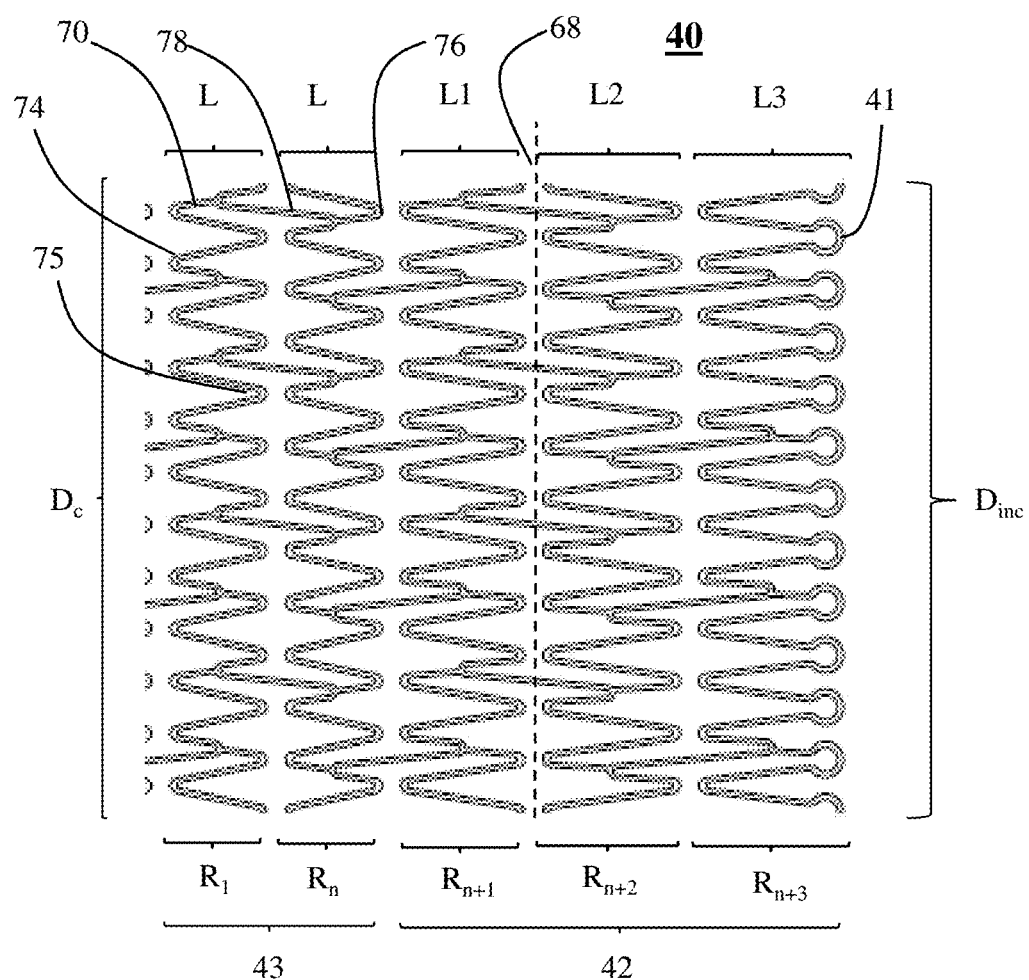
FIG. 4B is a schematic view of an embodiment of the support structure useful to construct the region proximal to the first region of a vascular graft shown in FIGS. 1A and 1B, according to one aspect of the present invention.

The present invention is directed to various embodiments of a radial support graft device and/or stent-graft useful for various vascular access applications, including but not limited facilitating vascular access in vascular bypass applications, facilitating treatment of atherosclerosis and facilitating arterial venous access for dialysis treatment. In an exemplary embodiment, the devices of the present invention have an expandable flared end, bifurcated design, and/or stent (i.e., radial support structure) pattern configured to facilitate vascular access and substantially sutureless and secure implantation of the device into the vasculature of a patient. Although the present invention will be described with reference to the figures, it should be understood that many alternative forms can embody the present invention. One of skill in the art will additionally appreciate different ways to alter the parameters disclosed, such as the size, shape, or type of elements or materials, in a manner still in keeping with the spirit and scope of the present invention.

Referring now to the exemplary embodiments shown in FIGS. 1A through 17C, wherein like parts are designated by like reference numerals throughout, these figures illustrate example embodiments of a vascular graft, and methods of producing and using the same according to the present invention. In particular, these embodiments show a vascular graft (e.g., for anastomosis) having an outflow region capable of being expanded, for example, after implantation into a body passageway (e.g., a blood vessel) to restore patency, and methods for using and producing the same.

A vascular graft 10, in accordance with an exemplary embodiment of the present invention, is illustrated in FIG. 1A. Vascular graft 10 is configured as a conduit 20 having a hollow body region 43 with an internal lumen 21 formed by wall 30. The conduit 20 comprises at least one inflow aperture 32 at an inflow end 35 and an outflow aperture 34 at an outflow end 36 of an outflow region 42 opposite from the at least one inflow aperture 32. The inflow end 35 and outflow end 36, of the conduit 20 are in fluid communication with each other via internal lumen 21, which is defined conduit 20 and extends between the at least one inflow aperture 32 and the outflow aperture 34. The wall 30 of conduit 20 is formed by a support structure 40 and a biocompatible layer 50. Support structure 40 may be any device configured to maintain patency of a vessel. Exemplary support structures 40 may include stents. In one embodiment support structure 40 may be an expandable structure and constructed from a shape memory alloy, such as nitinol. In an exemplary embodiment, a biocompatible layer 50, which may be configured as a cover, sheath or sleeve, may at least partially or fully cover an exterior surface of support structure 40. The support structure 40 may be separate from the biocompatible layer 50, adhered to the biocompatible layer 50, at least partially embedded in the material of the biocompatible layer 50, or any permutation of the foregoing. The support structure 40 along the outflow region 42 is under continuous compressive stress (S) resulting from a continuous applied load caused by the biocompatible layer 50 against the support structure 40. For example, the support structure 40 may be arranged to springingly or resiliently exert a continuous radially outwardly directed force against the biocompatible layer 50, which biocompatible layer 50 correspondingly exerts the continuous compressive stress on the support structure 40.

FIGS. 2A, 2B, and 2C show views of the support structure 40 of the vascular graft 10 shown in FIG. 1A, illustrating the support structure 40 prior to combination with a biocompatible layer 50 to form wall 30 (FIG. 2A), after combining the support structure 40 shown in FIG. 2A with the biocompatible layer 50 to form wall 30 (FIG. 2B), and after expanding the outflow region 42 of the support structure 40 of the vascular graft 10 shown in FIG. 2B (FIG. 2C).

In FIG. 2A, the support structure 40 prior to combination with the biocompatible layer 50 to form the wall 30 conduit 20 has varying outer diameter along the length of support structure 40. As shown, support structure 40 has a constant effective outer diameter measurement $D_c$ along the body region 43, and a radially and outwardly flaring effective outer diameter measurement $D_{inc}$ that increases along at least a portion of the outflow region 42 towards outflow aperture 34 to give the outflow region a "flared" shape or appearance, as discussed further below. This outwardly flared configuration of support structure 40 allows for substantially sutureless attachment and retention of stent graft 10 within the vasculature of a patient. Upon covering the support structure 40 with biocompatible layer 50, as show in FIG. 2A, the flared outflow region 42 is constricted such that conduit 20 is reshaped to have a constant effective outer diameter measurement $D_c$ along the length of body region 43 and outflow region 42, as shown in FIG. 2B. In an exemplary embodiment, outflow region 42 is constructed from a shape-memory alloy, such as a nitinol, that is capable of expanding from its constrained state to achieve and maintain a flared configuration upon application of an expansion force, such as balloon catheter expansion. This shape memory support structure 40 may be self-expanding, but is unable to assume its flared state without balloon expansion due to the compressive stress applied by biocompatible layer 50. 2C shows the expanded effective outer diameter measurement $D_{exp}$ of the support structure 40 after an external expansion force is applied to the outflow region 42 of the support structure 40 in FIG. 2B.

FIGS. 3A-3O, show various example embodiments of the outflow region 42 of support structure 40, depicting various flared configurations. These illustrations represent the wire-frame profile of the support structure 40, without depiction its strut pattern. Those skilled in the art will appreciate that a number of different strut patterns can be utilized, and that all such patterns are considered as falling within the scope of the profiles depicted. With regards to FIGS. 3K-3O, those skilled in the art will additionally appreciate that the diameter of each support structure segment along the support structure 40 in the outflow region 42 may be different, depending on the particular implementation. In the example embodiment of FIGS. 3K and 3M, each of the support structure segments is generally constructed from a single zigzag ring (as explained below), such that the support structure segments form a conduit having stepwise increments that increase in diameter as they approach outflow aperture 34. In another example embodiment, support structure 40 may include a plurality of these stepwise increments at a sufficiently frequent intervals such that a portion of outflow region 42, i.e. the portion between a proximal and distal end of outflow region 42, appear to have a substantially uniform linear change in diameter (e.g. FIG. 3A), or alternatively a curvilinear change in diameter (e.g., FIGS. 3F and 3I), rather than a stepwise change in diameter. In yet another example embodiment the increments can occur in such a way that the effective outer diameter does not change along at least one segment along the support structure 40 in the outflow region 42 (e.g., FIGS. 3B, 3C, 3G, 3J, 3L, 3M, 3N, and 3O). In certain example embodiments the increments can occur in such a way that combines any of the configurations above (e.g., FIGS. 3L, 3N). Those skilled in the art can readily envision other suitable flared configurations that may be considered to fall within the scope of the present invention.

Turning now to FIG. 4, there is illustrated a wire frame design forming an exemplary support structure 40 construction at outflow region 42. FIG. 4 shows a properly scaled illustration of the support structure 40 showing the precise relative proportions of the support structure pattern depicted therein in a flat orientation. As shown, the support structure 40 is constructed of a series of interconnected rings (e.g., $R_1$, $R_n$, $R_{n+1}$, $R_{n+2}$, $R_{n+3}$, where n=an integer representing), each comprising a substantially zigzag shape comprising a series of peaks and valleys. Once the flattened wire frame is rolled into a three dimensional cylindrical configuration, the peaks or crowns of each ring directly faces and is aligned with a corresponding valley of an adjoining ring and vice versa. This peak to valley arrangement is present throughout the length of support structure 40 and creates a flexible structure, allowing stent 20 to bend and turn when implanted. FIG. 4 illustrates an exemplary strut or stent pattern of support structure 40.

In the example shown in FIG. 4, the support structure 40 in the outflow region 42 has an effective outer diameter measurement $D_{inc}$ that is incrementally greater at each segment (D, D$_1$, D$_2$, D$_3$) along the support structure 40 for each incrementally more distal portion or segments extending from the at least one inflow aperture 32 to the at least one outflow aperture 34. In this non-limiting example, the support structure 40 can be constructed of a series of interconnected rings (e.g., R$_1$, R$_n$, R$_{n+1}$, R$_{n+2}$, R$_{n+3}$, where n=an integer representing), each comprising a substantially zigzag shape. By way of example, in one embodiment, rings R$_1$ and R$_n$ of the support structure 40 are located in the body region 43 proximal to the outflow region 42, whereas rings R$_3$, R$_4$, and R$_5$ are located in the outflow region 42, with R$_5$ forming an edge of outflow aperture 34. Rings R$_1$ and R$_n$ of body region 43 may have the same size and dimension D. Whereas the rings in the body region 43 are generally have the same size and dimension, rings R$_3$, R$_4$, and R$_5$ have incrementally increasing width of a ring (i.e. lengths of the peaks and valleys) D1, D2, and D3. The effective outer diameter measurement of the support structure 40 increases at each ring segment R as the width of each ring segment D increases. For example, the width D1 of ring segment R3 is greater than the width D of ring segment R$_n$, thereby increasing the effective outer diameter measurement of the support structure 40 at ring segment R$_3$ relative to ring segment R$_n$, the width D$_2$ of ring segment R$_4$ is greater than the width D$_1$ of ring segment R$_3$, thereby increasing the effective outer diameter measurement of the support structure 40 at ring segment R$_4$ relative to ring segment R$_3$, and the width D$_3$ of ring segment R$_5$ is greater than the width D$_2$ of ring segment R$_4$, thereby increasing the effective outer diameter measurement of the support structure 40 at ring segment R$_5$. The effective outer diameter measurement of this embodiment of support structure 40 in the outflow region 42 therefore is incrementally greater at each segment along the support structure 40 that is incrementally more distal form the at least one inflow aperture 32. Although there is shown only 3 ring segments R$_{n+1}$, R$_{n+2}$, and R$_{n+3}$ with incrementally increasing dimensions D1, D2, and D3, respectively, it is to be understood that the outflow region 42 of the support structure 40 can be provided with more (e.g., 4, 5, 6, etc.) or less (e.g., 2) ring segments R depending on the particular application, as will be appreciated by those skilled in the art.

As shown in the embodiments illustrated in FIGS. 3A-3O (described above), any particular segment R (R$_{n+1}$, R$_{n+2}$, R$_{n+3}$) having width D (D$_1$, D$_2$, D$_3$) can be provided with a constant effective outer diameter measurement D$_c$. In such embodiments, the support structure 40 flares at each location in the outflow region 42 in which the effective outer diameter measurement increases and does not flare at each location in which the effective outer diameter measurement remains constant. In some embodiments, the support structure 40 flares initially, for example, at segment R$_{n+1}$ due to an incrementally greater width D1 relative to width D of R$_n$, and then levels off at the outflow end 36, for example due to a constant effective outer diameter measurement due of the support structure at segments R$_{n+1}$ and R$_{n+2}$ (i.e. FIGS. 3B-3C). Those skilled in the art will readily appreciate that the length of the initial flare or leveled off section of the outflow region 42 can vary as desired by increasing the widths D1, or D2 and D3, respectively. In certain embodiments illustrated in FIGS. 3A through 3O (described above), any particular segment R (R$_{n+1}$, R$_{n+2}$, R$_{n+3}$) having width D (D1, D2, D3) can be provided with an effective outer diameter measurement that increases at a greater rate relative to a previous segment R. In certain embodiments illustrated in FIGS. 3A through 3O (described above), any particular segment R (R$_{n+1}$, R$_{n+2}$, R$_{n+3}$) having width D (D1, D2, D3) can be provided with an effective outer diameter measurement that increases at a lesser rate relative to a previous segment R. It should be appreciated by those of skill in the art that the flared outflow region 42 can be configured to alter the size and or shape of its flared appearance, as long as the effective outer diameter measurement of the support structure 40 prior to combination with the biocompatible layer 50 to form the wall 30 increases along at least a portion of the outflow region 42. Those skilled in the art will appreciate that the appearance (e.g., size, shape, or angle) of the flare in the outflow region 42 depends, in part, on the widths D1, D2, D3 of each ring segment R$_{n+1}$, R$_{n+2}$, R$_{n+3}$, respectively.

Various dimensions D (e.g., D, D1, D2, D3) for ring segments R (e.g., R$_1$, R$_n$, R$_{n+1}$, R$_{n+2}$, R$_{n+3}$) are contemplated for the support structure 40. Table 1 below provides non-limiting examples of dimensions for manufacturing a support structure 40 having an incrementally increasing effective outer diameter measurement D$_{inc}$ in the outflow region 42.

TABLE 1

Dimensions for Exemplary Ring Segments R$_{n+1}$, R$_{n+2}$, R$_{n+3}$

| Constant Effective Outer Diameter Measurement | D (R$_1$ – R$_n$) | D1 (R$_{n+1}$) | D2 (R$_{n+2}$) | D3 (R$_{n+3}$) | Maximum Effective Outer Outflow Diameter (Uncovered) |
|---|---|---|---|---|---|
| 6.0 mm | 2.18 mm +– 0.45 mm | 2.51 mm +– 0.45 mm | 2.88 mm +– 0.45 mm | 3.10 mm +– 0.45 mm | 11.4-11.6 mm |
| 7.0 mm | 2.04 mm +– 0.45 mm | 2.35 mm +– 0.45 mm | 2.70 mm +– 0.45 mm | 2.90 mm +– 0.45 mm | 12.4-12.6 mm |
| 8.0 mm | 1.89 mm +– 0.45 mm | 2.17 mm +– 0.45 mm | 2.50 mm +– 0.45 mm | 2.69 mm +– 0.45 mm | 13.4-13.6 mm |

In the exemplary embodiment shown in FIGS. 8A-8G outlet region 42 has the same flarable configuration, as shown in FIGS. 1A-2C and as discussed generally above. The inlet region 44 of this alternative stent graft 10 may have a pre-fabricated and pre-extended flared configuration prior to implant, as shown in FIGS. 8A-8G. Various views of this stent graft embodiment in which support structure 40 has a pre-fabricated and pre-extended outwardly flaring inflow region 44 for maintaining or improving patency of the graft along inflow region 44. In these examples, the flared shape or appearance is oriented in the opposite direction from the flared shape or appearance at outflow end 36. This pre-fabricated and pre-extended flared configuration of inflow region 44 facilitates friction fitted attachment and positioning within a vasculature.

Figure 8D:
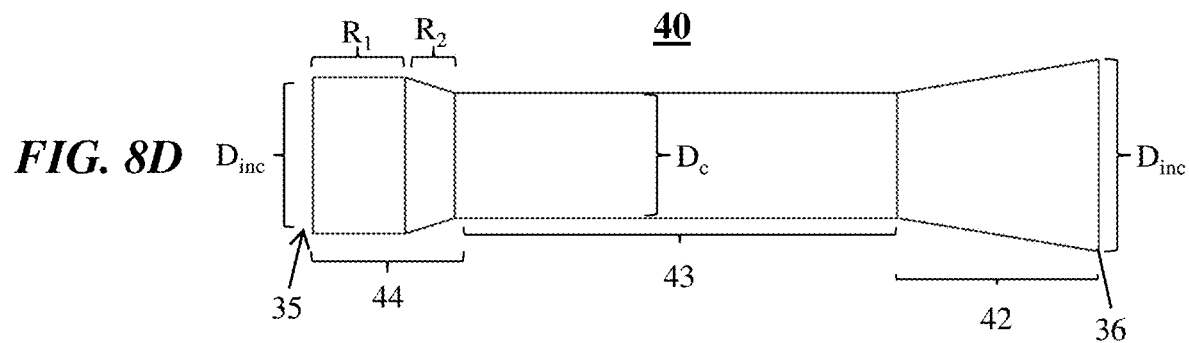
FIG. 8D is side wireframe view of the support structure shown in FIG. 8C, according to one aspect of the present invention.
Figure 8E:
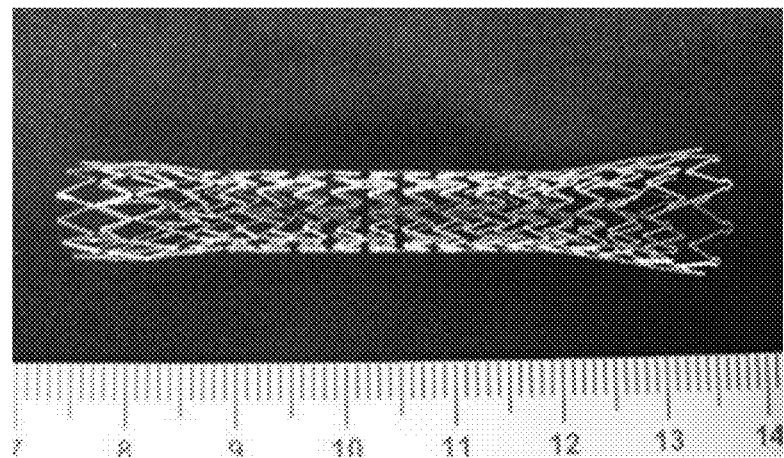
FIG. 8E is a photograph of the embodiment of the support structure shown in FIGS. 8A through 8D, according to one aspect of the present invention.

FIG. 8A shows a side view of the straight vascular graft shown in FIG. 1A, illustrating the flared configuration of the inflow region 44 of the support structure 40 prior to combination with the biocompatible layer 50 to form wall 30. FIG. 8B shows a schematic view of the straight vascular graft shown in FIG. 1A, illustrating the pre-fabricated, pre-extended flared configuration of the support structure 40 along the inflow region 44 and expandable out flow region 42 after combining the support structure 40 shown in FIG. 8A with the biocompatible layer 50 to form the wall 30. FIG. 8B shows the vascular graft after inflow region 44 has been expanded. FIG. 8C shows a schematic view of the straight vascular graft shown in FIG. 1A, illustrating the expanded effective outer diameter measurement $D_{exp}$ of the support structure 40 along the outflow region 42. FIG. 8D shows a side wireframe view of the support structure 40 shown in FIGS. 8A and 8D. FIG. 8E is a photograph showing an actual construction of the support structure 40 shown in FIG. 8A.

With particular reference to FIG. 8E, it is evident that the pre-fabricated, pre-expanded flared shape or appearance of the inflow region 44 is achieved by a similar design methodology to the one described in FIG. 4 in which ring segments $R_1$ and $R_2$ of the support structure 40 are provided with different widths D2, D1, respectively, from each other, as well as different widths D from the ring segments $R_3$ to $R_n$, where n=an integer. The different widths D (e.g., D2, D1, D) of ring segments R (e.g., $R_1$, $R_2$, $R_3$ to $R_n$, where n=an integer) impart the effective outer diameter measurements $D_{inc}$ which provide the support structure 40 along the outflow region 42 with a flared appearance.

Figure 8F:
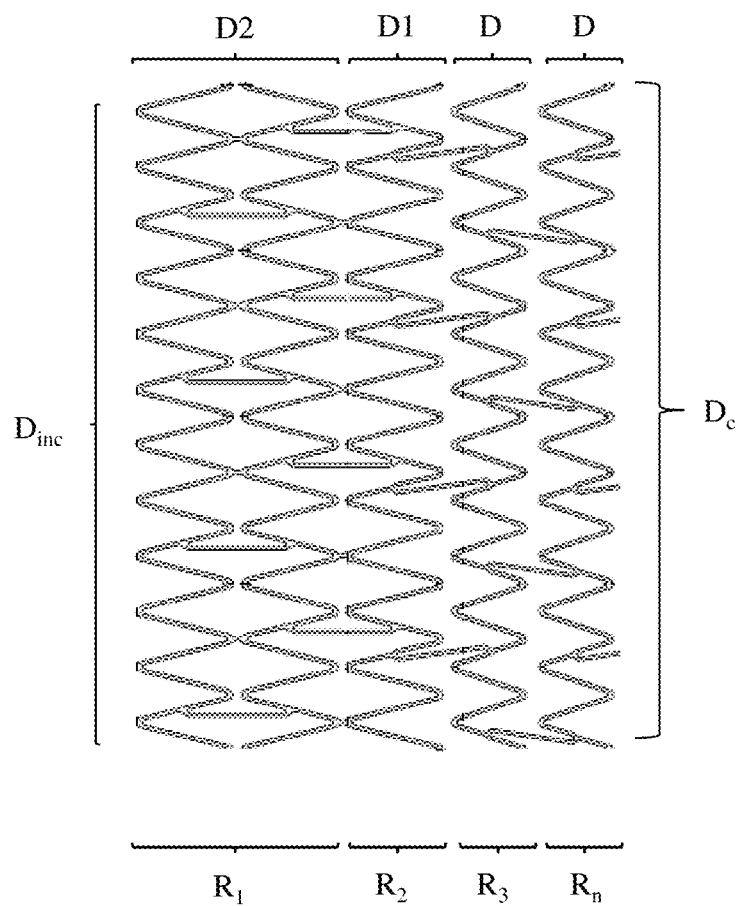
FIG. 8F is a schematic view of an embodiment of the support structure proximal to the inflow region of a vascular graft shown in FIGS. 8A, 8D and 8E, according to one aspect of the present invention.

The outflow region 42 of support structure 40 may be configured in the same manner as that discussed above and shown in FIG. 4B. FIG. 8F shows a schematic view of the support structure 40 useful for inflow region 44 according to an exemplary construction. The construction can be utilized for at least two objectives. In a first embodiment, the flared inflow region 44 creates a pre-fabricated, pre-expanded flared configuration prior to implant. In another embodiment, the pre-expanded and flared configuration provides a locally increased inside diameter that provides space for receiving (e.g., as in a socket) a lumen distinct from biocompatible layer 50, although possibly constructed of the same base material as biocompatible layer 50. For example, an extension lumen 51 having a wall thickness that is thicker than layer 50 may be inserted into the constructed socket such that the inner luminal surface of the extension lumen 51 will be substantially flush with or at least the same approximate diameter as the inner luminal surface of conduit body portion 43.

FIG. 8F shows a scaled illustration of the support structure 40 showing the precise relative proportions of the support structure pattern depicted therein. Each ring forming conduit body portion 43 comprises a series of peaks and valleys, best shown as $R_n$ and $R_3$ in FIG. 8F. The peaks or crowns of each of these rings directly face and are aligned with a corresponding valley of an adjoining ring, and struts connecting adjoining rings builds flexibility into the graft to facilitate in-situ bending. A proximal inflow region 35 of support structure 40 includes a plurality of rings in which the peaks or crowns of a ring $R_2$ faces the peaks and crowns of adjoining rings $R_1$ while the valleys of ring R2 directly faces and aligns with valleys of adjoining rings $R_1$ to provide additional stiffness at inflow region 35.

As is shown in FIG. 8F, ring segments $R_1$ and $R_2$, which are located proximal to the inflow end 35 of the inflow region 44 of the support structure 40, are provided with greater widths $D_2$, $D_1$, respectively, than ring segments $R_3$ to $R_{n\ (where\ n=an\ integer)}$, which are located in the body region 43 of support structure 40. Providing ring segment $R_2$ with a greater width $D_1$ than the width D of ring segment $R_3$ causes the wall 30 adjacent to ring segment $R_2$ to flare outward as illustrated by the angled $R_2$ segment shown in FIG. 8D. The effective outer diameter measurement $D_{inc}$ of the inflow region 44 shown in this example consists of ring segment $R_1$ which comprises a constant effective outer diameter measurement along its width $D_2$, as is illustrated by the line extending along the longitudinal width of ring segment R1 shown in FIG. 8D. It should be appreciated by those skilled in the art, however, that the support structure 40 proximal to the inflow region 44 can be configured in any desirable manner which maximizes patency of the inflow region while vascular graft 10 is implanted in a body lumen.

Looking now at FIGS. 2B and 8B, there is shown a schematic view of an embodiment of the vascular graft 10 shown in FIGS. 1A and 8A depicting the generally uniform effective outer diameter measurement of the support structure 40 after combining the support structure 40 shown in FIGS. 2A and 8A with the biocompatible layer 50 to form the wall 30. Application of biocompatible layer 50 to an exterior surface of support structure 40 so as to form wall 30 places the support structure 40 in the outflow region 42 under continuous compressive radial stress S (e.g., radial compressive stress) resulting from a continuous applied load to support structure 40 by compressing the biocompatible layer 50 against the support structure 40. Generally, the compressive stress S resulting from the continuous applied load in the outflow region 42 is greater than a compressive stress $S_0$ resulting from the applied load in the body region 43. Those skilled in the art will appreciate that the compressive stress S resulting from the continuous radially applied load in the outflow region 42 generally changes along the length of outflow region 42 as the effective outer diameter of the support structure 40 in the outflow region 42 changes. As is shown in FIGS. 2B and 8B, for example, the compressive stress S experienced by the support structure 40 resulting from the continuous applied load in the outflow region 42 incrementally increases along the length of support structure 40 as it approaches outflow aperture 34, i.e. compressive stress S is greater at each segment along the support structure 40 that is incrementally more distal from the at least one inflow aperture 32 at the inflow end 35. In this example, the compressive stress S is at a minimum $S_{min}$ at a proximal area of outflow region 42 and increases, as the effective outer diameter of the support structure 40 (prior to combination with the biocompatible layer 50 to form wall 30) increases, to a maximum compressive stress $S_{max}$ proximal to the outflow end 36.

The compressive stress S causes an elastic deformation of the support structure 40 in the outflow region 42. As will be appreciated by those skilled in the art, the extent of the elastic deformation is a function of the compressive stress S resulting from the applied load caused by the biocompatible layer 50. In the example shown in FIGS. 2B and 8B, the elastic deformation of the support structure 40 in the outflow region 42 is incrementally greater at each segment along the support structure 40 that is incrementally more distal from the at least one inflow aperture 32, as illustrated by the increasing compressive stress from a minimum compressive stress $s_{min}$ to a maximum compressive stress $S_{max}$.

In contrast to the deformation inducing compressive stress S along the outflow region 42, a compressive stress $S_0$ resulting from an applied load by biocompatible layer 50 at inflow distal end 35 and body region 43 causes only negligible elastic deformation of the support structure 40 along the body region 43. For the sake of clarity, it is to be understood by those skilled in the art that the negligible compressive stress $S_O$ experienced by the support structure 40 in the body region 43 resulting from the applied load caused by the biocompatible layer 50 against the support structure 40 is negligible relative to the amount of compressive stress S ($S_{min}$ to $S_{max}$) experienced by the support structure 40 in the outflow region 42 resulting from the applied load caused by the biocompatible layer 50 against the support structure 40. As used herein, negligible compressive stress $S_O$ refers to an amount of compressive stress that is not accompanied by or associated with a change in the effective outer diameter, or is accompanied by or associated with only a very minor amount of change in the effective outer diameter, of the portion or region of the support structure 40 experiencing the compressive stress S, as will be appreciated by those skilled in the art. In contrast to the negligible compressive stress $S_O$ experienced by the support structure 40 in the body region 43 after combination with the biocompatible layer 50 to form wall 30, the support structure 40 in the outflow region 42 after combination with the biocompatible layer 50 to form wall 30 experiences a substantial amount of compressive stress that generally changes as the effective outer diameter measurement of the support structure 40 prior to combination with biocompatible layer 50 to form wall 30 changes. As used herein, "substantial compressive stress" and "continuous compressive stress" are used interchangeably herein to mean an amount of compressive stress that is accompanied by or associated with a change in the effective outer diameter of the portion or region of the support structure 40 experiencing the compressive stress S in the radial direction, as will be appreciated by those skilled in the art.

The combination of the incrementally greater elastic deformation of the support structure 40 along the outflow region 42 with the absence of elastic deformation of the support structure 40 along the body region 43 imparts the conduit 20 with a uniform effective outer diameter measurement, as is illustrated in FIGS. 2B and 8B. This effective outer diameter measurement comprises a constant effective outer diameter measurement $D_c$ along the body region 43 and a constrained effective outer diameter measurement $D_{con}$ along the outflow region 42. As used herein, "constrained" in connection with "effective outer diameter measurement" refers to the effective outer diameter measurement of the support structure 40 along the outflow region 42 under the compressive stress S relative to the effective outer diameter measurement of the support structure 40 along the outflow region 42 in the absence of compressive stress S prior to combination of the support structure 40 with the biocompatible layer 50 to form the wall 30. The constrained effective outer diameter measurement $D_{con}$ is approximately equal to the constant effective outer diameter measurement $D_c$. Notably, the compressive stress S resulting from the continuous applied load maintains the support structure 40 along the outflow region 42 at the constrained effective outer diameter measurement $D_{con}$.

The elastic deformation of the support structure 40 along the outflow region 42 is reversible. The extent to which the elastic deformation of the support structure 40 along the outflow region 42 can be reversed depends on a variety of factors, including the length D (e.g., D1, D2, D3) of each ring segment R (e.g., $R_{n+1}$, $R_{n+2}$, $R_{n+3}$), and the amount of counter force applied to the support structure 40 in the outflow region 42, as will be appreciated by those skilled in the art. In this regard, a counter force comprising a radial expansion force applied to the support structure 40 in the outflow region 42 causes plastic deformation of the biocompatible layer 50. Such counter force causes a reduction of the compressive stress S experienced by the support structure 40. In other words, as the counter force increases the plastic deformation of the biocompatible layer 50, the compressive stress S experienced by the support structure 40 decreases, reversing the plastic deformation of the support structure 40.

Focusing now on FIGS. 2C and 8C, there is shown a schematic view of an embodiment of the vascular graft 10 shown in FIGS. 1A and 8A depicting the expanded effective outer diameter measurement $D_{exp}$ of the support structure 40 of the vascular graft shown in FIGS. 2B and 8B, after expanding the outflow region 42 of the support structure 40. As noted above, the expanded effective outer diameter measurement $D_{exp}$ of the support structure 40 along the outflow region 42 results upon application of a counter force comprising a radial expansion force. The present invention contemplates the use of any suitable means for applying such radial expansion force, for example, by advancing a radially expandable device (e.g., a balloon catheter 98) along the internal lumen of the conduit 20 from the at least one inflow aperture 32 toward the outflow aperture 34 and expanding the radially expandable element. Other suitable means for applying such radial expansion force are apparent to the skilled artisan.

Those skilled in the art will further appreciate that the present invention contemplates the use of any amount of counter force comprising a radial expansion force which is capable of overcoming the continuous applied load contributed by the biocompatible layer 50 and thus permits expanding the outflow region 42. Preferably, the amount of counter force comprising the radial expansion force used is an amount that results in the atraumatic expansion of the outflow region 42 within a body lumen. Exemplary ranges of such counter forces will be apparent to the skilled practitioner. For the sake of clarity, however, an exemplary range of counter forces which can result in the atraumatic expansion of the outflow region 42 in vivo or in situ includes those counter forces which arise from using a semi-compliant balloon that is no more than 2.5 mm (more preferably no more than 2.0 mm) over the effective outer diameter measurement of the outflow region 42.

Following application of a counter force comprising a radial expansion force applied to the support structure 40 in the outflow region 42, the graft reconfigures in such a way as to result in a plastically deformed biocompatible layer 50. In some instances, following application of a counter force, the vascular graft 10 reconfigures in such a way as to result in a plastically deformed biocompatible layer 50 and a compressive stress S experienced by the support structure 40 that is less than the compressive stress S experienced by the support structure prior 40 to application of the counter force. In some instances, following application of a counter force, the graft reconfigures in such a way as to result in the support structure 40 experiencing residual compressive stress S where there was previously continuous compressive stress S (e.g., substantial compressive stress) experienced by the support structure 40 prior to application of the counter force. As used herein, "residual compressive stress" means an amount of compressive stress S that remains partially as a result of recoil associated with plastic deformation of the biocompatible layer 50 upon application of the counter force comprising the radial expansion force. Those skilled in the art will appreciate that the amount of such residual compressive stress depends on a variety of factors, including the magnitude of the radial expansion force and the amount of compressive stress S experienced by the support structure 40 due to the continuous applied load caused by the biocompatible layer 50 against the support structure 40 before application of the counter force, for example.

Still looking at FIGS. 2C and 8C, it is evident that a counter force comprising a radial expansion force applied to the support structure 40 in the outflow region 42 reconfigures the support structure 40 in to the outflow region 42 from the constrained effective outer diameter measurement $D_{con}$ shown in FIGS. 2B and 8B to an expanded effective outer diameter measurement $D_{exp}$ shown in FIGS. 2C and 8C that is greater than the constrained effective outer diameter measurement $D_{con}$ along at least a portion of the support structure 40 in the outflow region 42. In one embodiment, the change in diameter between the constrained effective outer diameter measurement $D_{con}$ and the expanded effective outer diameter measurement $D_{exp}$ is about 0.5 mm to about 2.5 mm or about 1 mm to about 2 mm, and even more 1 mm to 1.5 mm. In accordance with another example embodiment, the expanded effective outer diameter measurement $D_{exp}$ is at least 1 mm greater than the constrained effective outer diameter measurement $D_{con}$ along at least a portion of the support structure 40 in the outflow region 42. Of course, the expanded effective outer diameter measurement $D_{exp}$ can be at least 1.10 mm, at least 1.20 mm, at least 1.30 mm, at least 1.40 mm, at least 1.50 mm, at least 1.60 mm, at least 1.70 mm, at least 1.80 mm, at least 1.90 mm, at least 2.0 mm, at least 2.10 mm, at least 2.20 mm, at least 2.30 mm, at least 2.40 mm, at least 2.50 mm, at least 2.60 mm, at least 2.70 mm, at least 2.80 mm, at least 2.90 mm, at least 3.0 mm, at least 3.10 mm, at least 3.20 mm, at least 3.30 mm, at least 3.40 mm, at least 3.50 mm, at least 3.60 mm, at least 3.70 mm, at least 3.80 mm, at least 3.90 mm, at least 4.0 mm, at least 4.10 mm, at least 4.20 mm, at least 4.30 mm, at least 4.40 mm, at least 4.50 mm, at least 4.60 mm, at least 4.70 mm, at least 4.80 mm, at least 4.90 mm, or 5.0 mm or more greater than the constrained effective outer diameter measurement $D_{con}$ along at least a portion of the support structure 40 in the outflow region 42, depending on various factors, such as magnitude and duration of the radial expansion force and the length D (e.g., D1, D2, D3, etc.) or amount of ring segments R (e.g., $R_{n+1}$, $R_{n+2}$, $R_{n+3}$, etc.) as will be appreciated by those skilled in the art. In accordance with another example embodiment, the expanded effective outer diameter measurement $D_{exp}$ of the support structure 40 along the outflow region 42 after being reconfigured is at least 1.0 mm greater than the constrained effective outer diameter measurement $D_{con}$ along the entire portion of the support structure 40 in to the outflow region 42. In certain example embodiments, the expanded effective outer diameter measurement $D_{exp}$ can be at least 1.10 mm, at least 1.20 mm, at least 1.30 mm, at least 1.40 mm, at least 1.50 mm, at least 1.60 mm, at least 1.70 mm, at least 1.80 mm, at least 1.90 mm, at least 2.0 mm, at least 2.10 mm, at least 2.20 mm, at least 2.30 mm, at least 2.40 mm, at least 2.50 mm, at least 2.60 mm, at least 2.70 mm, at least 2.80 mm, at least 2.90 mm, at least 3.0 mm, at least 3.10 mm, at least 3.20 mm, at least 3.30 mm, at least 3.40 mm, at least 3.50 mm, at least 3.60 mm, at least 3.70 mm, at least 3.80 mm, at least 3.90 mm, at least 4.0 mm, at least 4.10 mm, at least 4.20 mm, at least 4.30 mm, at least 4.40 mm, at least 4.50 mm, at least 4.60 mm, at least 4.70 mm, at least 4.80 mm, at least 4.90 mm, or 5.0 mm or more greater than the constrained effective outer diameter measurement $D_{con}$ along the entire portion of the support structure 40 in the outflow region 42, as will be appreciated by those skilled in the art.

The support structure 40 can be constructed from any material that enables the support structure 40 in the outflow region 42 to reconfigure from a constrained effective outer diameter measurement $D_{con}$ to an expanded effective outer diameter measurement $D_{exp}$ upon application of the counter force. In accordance with one example embodiment, the support structure 40 is constructed from a shape memory alloy. Exemplary shape memory alloys can be formed from a combination of metals including, but not limited to: aluminum, cobalt, chromium, copper, gold, iron, nickel, platinum, tantalum, and titanium. In accordance with one example embodiment, the support structure 40 is constructed from nitinol. Other shape memory alloys or other materials which can be used to construct the support structure 40 are apparent to the skilled artisan.

Those skilled in the art will appreciate that the support structure 40 can be constructed with a larger or smaller expandable portion. The skilled artisan will also appreciate that the same methodology described above in connection with FIG. 3 which enables outflow region 42 to be expandable can be applied to render other portions of the support structure 40 expandable (e.g., the body region).

The biocompatible layer 50 can be constructed from any biocompatible material. The material may further be substantially impermeable to fluid in certain embodiments. The material is capable of causing a continuous applied load to place the support structure 40 under a sufficient continuous compressive stress (e.g., substantial compressive stress as defined herein) to maintain the constrained effective outer diameter measurement $D_{con}$ of the support structure 40 along the outflow region 42 after combining the support structure 40 with the biocompatible layer 50 to form the wall 30. In accordance with an example embodiment, the biocompatible layer 50 comprises an expandable polymer. In accordance with an example embodiment, the biocompatible layer 50 comprises expanded polytetrafluoroethylene (ePTFE).

Generally, as is shown in FIGS. 2B-2C and 8B-8C, the biocompatible layer 50 extends at least along the entire longitudinal length of the support structure 40 from the inflow end 35 to the outflow end 36. As will be appreciated by those skilled in the art, the biocompatible layer 50 may extend at least partially beyond, or fall short of, the inflow end 35 and the outflow end 36 in accordance with acceptable manufacturing specifications. In accordance with one example embodiment, the biocompatible layer 50 can extend beyond the edge of the inflow end 35 and the outflow end 36 and wrap around at least a portion of the interior surface of the support structure 40 in the form of a cuff.

Referring to FIGS. 5A, 5B, 5C and 5D, there are shown example cross-sections of vascular graft 10 shown in FIGS. 1A and 8A, depicting various ways in which the biocompatible layer 50 can be configured. As can be seen in the exemplary embodiments of FIGS. 5A and 5C, the biocompatible layer 50 can comprise a biocompatible outer layer 54 and a separate biocompatible inner layer 55 spaced apart therefrom such that outer layer 54 and inner layer 55 are positioned on opposite sides of support structure 40. As shown in FIGS. 5A and 5B, the biocompatible outer layer 54 and the biocompatible inner layer 55 can be configured as distinct layers of the same substrate continuously wrapped around an end of the support structure 40 or instead as two separate substrates (i.e., non-continuous) that are positioned at opposite sides of the support structure 40. In this example, either the biocompatible outer layer 54 or the biocompatible inner layer 55 may extend at least partially beyond and wrap around the edge of the inflow end 35 and outflow end 36 to form a cuff, for example, to minimize damage to surrounding tissue during deployment of the vascular graft 10. The circled portion of FIG. 5A is represented as FIG. 5B and shows an exploded view of a portion of the biocompatible layer 50 showing how the biocompatible outer layer 54 and the biocompatible inner layer 55 conform to each other and the support structure 40 as a result of how the layers may be applied, heated, sintered, or otherwise adhered on or to the support structure 40, methods of which are known to those of skill in the art. As shown in the example embodiment in FIG. 5B, the biocompatible layer 50 can comprise a biocompatible outer layer 54 without a biocompatible inner layer 55. Those skilled in the art will appreciate, however, that the biocompatible inner layer can help to decrease the likelihood of stenosis or occlusion in the conduit 20 of the vascular graft 10 or to alter the fluid impermeability of the wall 30. FIGS. 5A-5D show an example embodiment of the vascular graft 10 in which the biocompatible layer 50 encapsulates the support structure 40 with the biocompatible outer layer 54 and the biocompatible inner layer 55. In this example, the biocompatible outer layer 54 and the biocompatible inner layer 55 can be configured to encapsulate the support structure 40. All known methods and structures relating to the application or use of a biocompatible layer such as those described herein are anticipated for use in conjunction with the present invention, such that the form of the layer on the support structure is not limited by the particular illustrative examples provided herein.

In an exemplary embodiment, biocompatible layer 50 is configured as a sheath, sleeve or other covering that binds and applies a compressive stress to support structure 40. In an exemplary embodiment, biocompatible layer 50, particularly biocompatible outer layer 54, is adhesively bound to an exterior surface of support structure 40 forming a constricting and continuous covering over support structure 40. The covering may be constructed from any suitable biocompatible material, particularly ePTFE that is processed to apply a compressive force against support structure 40. In an exemplary embodiment, biocompatible layer 50, including biocompatible outer layer 54 and/or biocompatible inner 55 form hemocompatible coverings configured and adapted for engaging tissue and/or blood. It should be appreciated that the biocompatible layer 50 described herein is distinguishable from a mere surface modifying coating that is conventionally applied to medical devices for purposes of delivering a therapeutic agent or changing the surface characteristics of a medical device, for example, a hydrophilic coating. Nevertheless, it is contemplated that such surface-modifying coatings, for example a coating comprising a biological oil or fat, as is described in U.S. Pat. No. 8,124,127 (which is incorporated herein by reference in its entirety), can be used to coat at least a portion of a surface of the support structure 40 or the biocompatible outer 54 and inner 55 layers, for reasons that would be evident to those skilled in the art. For example, it may be desirable to coat at least a portion of the interior surface of support structure 40 or the biocompatible inner layer 55 with a cured fish oil coating containing an anti-clotting therapeutic agent to prevent or minimize occlusion of the implanted graft.

Turning now to FIG. 1B, an alternative embodiment of a vascular graft 10' is shown. Whereas the example shown in FIG. 1A depicts a straight vascular graft 10, the vascular graft 10' of FIG. 1B may be designed to include a second inflow aperture 33 to provide a bifurcated or generally T-shaped vascular graft 10', as is depicted in the example shown in FIG. 1B. It is to be understood that any description given with respect to components common to both of the grafts 10 and 10' (i.e., those components identified with the same reference numerals) is generally applicable to both of the embodiments, unless otherwise indicated. As is shown in FIG. 1B, a longitudinal axis of the second inflow aperture 33 intersects a longitudinal axis of the at least one inflow aperture 32 at a non-parallel angle. As used herein, "non-parallel angle" means an angle in which the longitudinal axis of the at least one inflow aperture 32 is not parallel to the longitudinal axis of the second inflow aperture 33 (e.g., greater than 0°). The non-parallel angle can be any non-parallel greater than 0° and less than 180° depending on the particular arrangement needed for the graft implantation. Preferably, the non-parallel angle at which the longitudinal axis of the second inflow aperture 33 intersects the longitudinal axis of the at least one inflow aperture 32 is between about 25° and about 45°. In accordance with one example embodiment, the non-parallel angle at which the longitudinal axis of the second inflow aperture 33 intersects the longitudinal axis of the at least one inflow aperture 32 is about 35°.

Figure 6A:
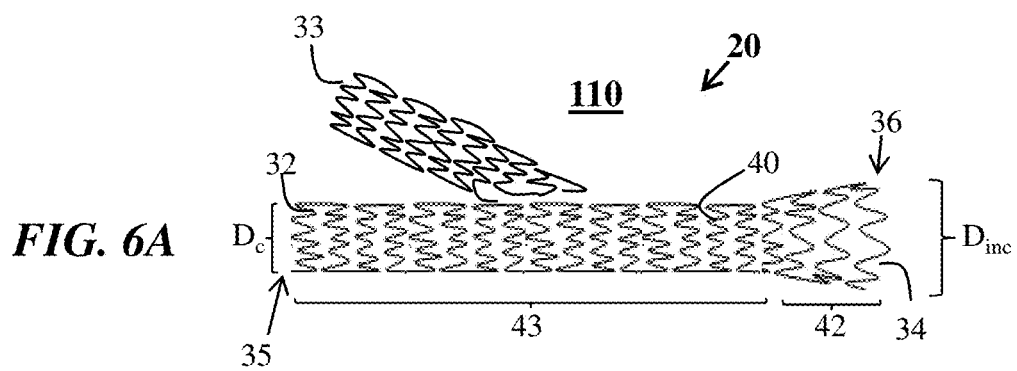
FIG. 6A is a side view of an embodiment of a support structure of the vascular graft shown in FIG. 1B, illustrating the support structure prior to combination with the biocompatible layer, according to one aspect of the present invention.
Figure 6B:
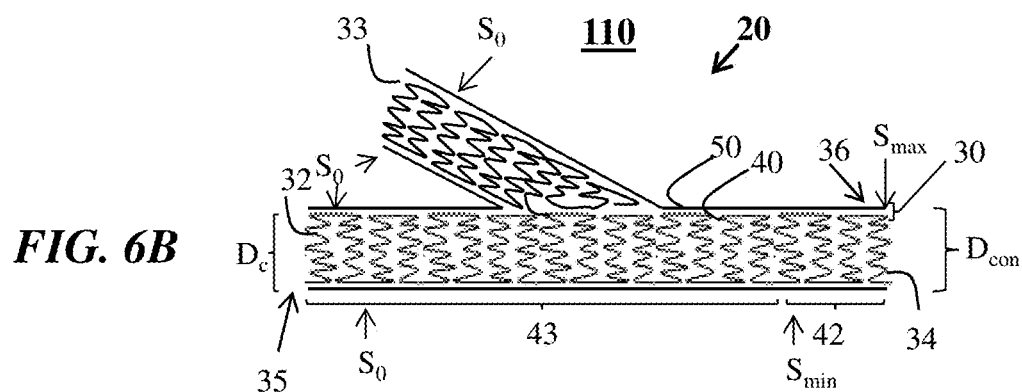
FIG. 6B is a schematic view of an embodiment of the vascular graft shown in FIG. 1B after combining the support structure shown in FIG. 6A with the biocompatible layer, according to one aspect of the present invention.
Figure 6C:
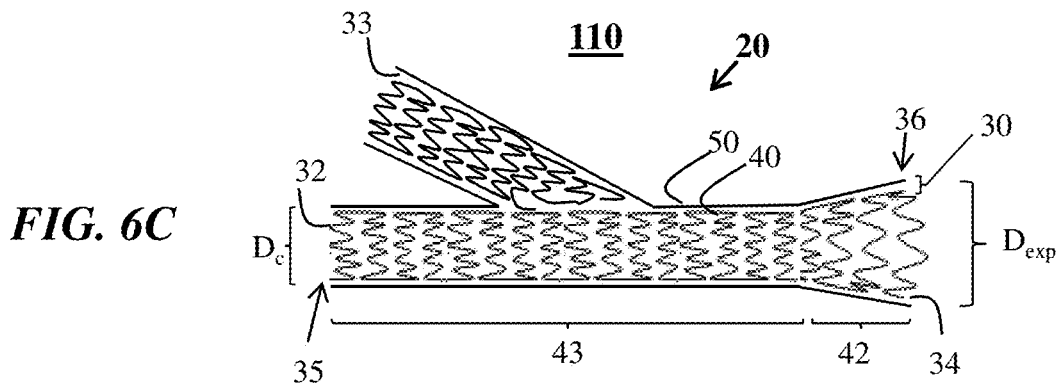
FIG. 6C is a schematic view of an embodiment of the vascular graft shown in FIG. 1B after expanding the outflow region of the support structure of the vascular graft shown in FIG. 6B, according to one aspect of the present invention.

FIGS. 6A, 6B, and 6C show various views of embodiments of a support structure 40 of the bifurcated vascular graft 110 construction shown in FIG. 1B, illustrating the support structure 40 prior to combination with the biocompatible layer 50 to form the wall 30 (FIG. 6A), after combining the support structure 40 shown in FIG. 6A with the biocompatible layer 50 to form wall 30 (FIG. 6B), and after expanding the outflow region 42 of the biocompatible layer 50 covered support structure 40 of the vascular graft 110 shown in FIG. 6B (FIG. 6C). Those skilled in the art will appreciate that the description of the structure, function, and components of the straight vascular graft 110 above in connection with FIGS. 2A-5C is equally applicable to the bifurcated vascular graft 110 shown in FIGS. 6A-6C.

Figures 7A, 7B, 7C:
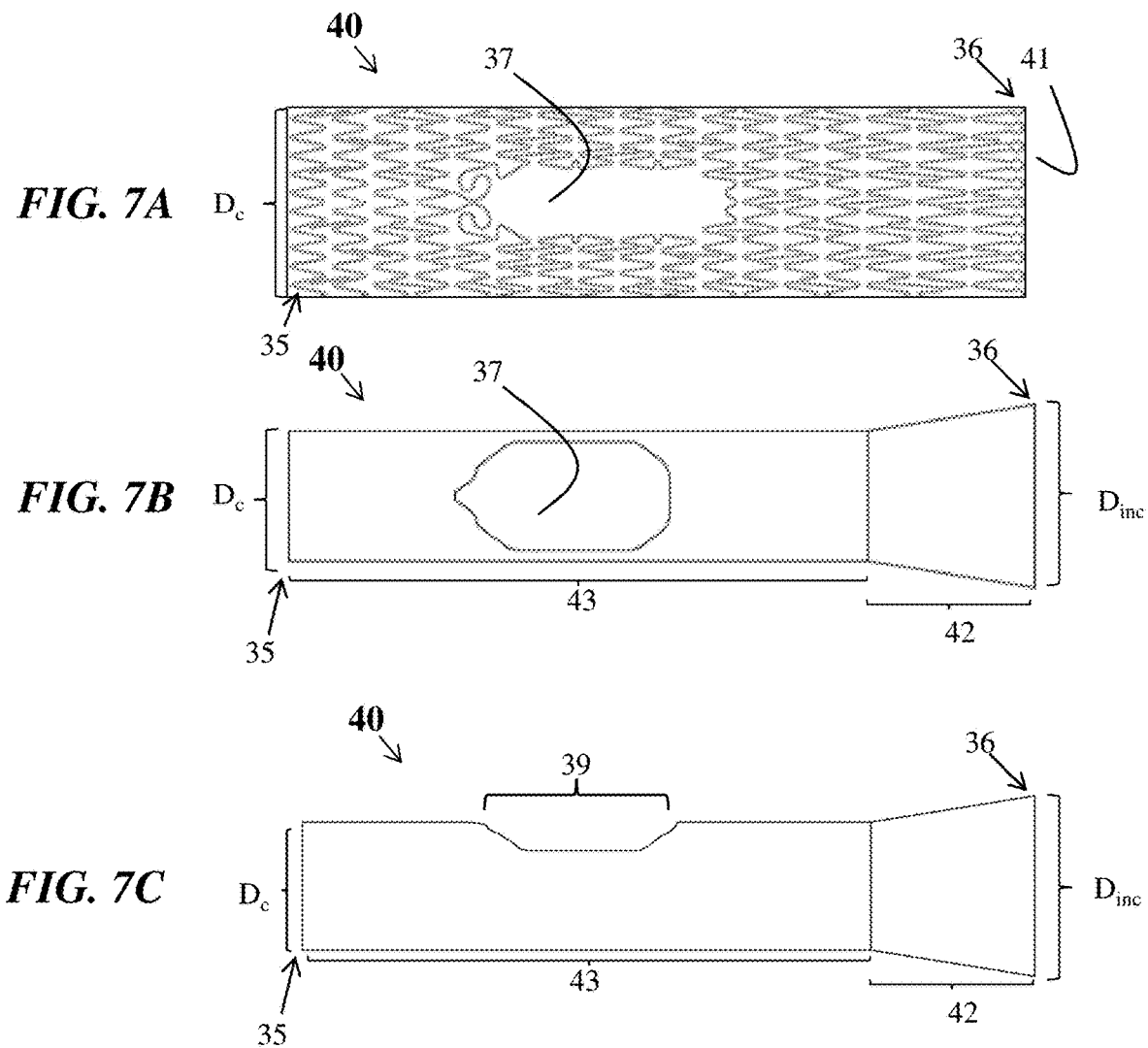
FIG. 7A is a top view of an embodiment of a support structure of the vascular graft shown in FIG. 1B.
FIG. 7B is a top wireframe view of the support structure of the vascular graft shown in FIG. 7A.
FIG. 7C is a side wireframe view of the support structure of the vascular graft shown in FIG. 7B.

Referring now to FIGS. 7A-7C, there is shown in a top view (FIG. 7A), a top wireframe view (FIG. 7B), and a side wireframe view (FIG. 7C) of an embodiment of a support structure of the vascular graft shown in FIGS. 1B, 6A-6C, depicting the support structure with only at least one inflow aperture 32 (see, e.g., FIG. 5A) and an outflow aperture 34 (see, e.g., FIG. 5C) before the second inflow aperture 33 is attached to the graft body to form the bifurcated vascular graft 10' shown in FIGS. 1B and 6A-6C. As will be appreciated by those skilled in the art, the support structure 40 featured in FIGS. 7A-7C includes all of the pertinent features of the vascular graft 10' shown in FIGS. 6A-6C. FIG. 7A shows a properly scaled illustration of the support structure 40 showing the precise relative proportions of the support structure and its strut/stent pattern. As shown in the example embodiment in FIGS. 7A-7B, the support structure also includes a junction aperture 37 to which a hollow branch conduit 99 is connected. Junction aperture 37 and the second inflow aperture 33 of branch conduit 99 is in fluid communication with the at least one inflow aperture 32 and outflow aperture 34. As is shown in the example in FIG. 7A, the support structure 40 can terminate in one or more blunt ends 41, for example, to prevent or minimize damage to the biocompatible layer 50 caused by the support structure 40. The blunt ends 41 can be formed in a keyhole like shape as shown in FIG. 7A, or any other shape which enables the blunt ends 41 to prevent or minimize damage to the biocompatible layer 50 by the support structure 40.

To facilitate attachment of the branch conduit 99 and its second inflow aperture 33 to the body region 43 of the support structure 40 at junction aperture 37, a depression 39 is provided in the contour of the body region 43 of support structure 40, as is illustrated in the example embodiment in FIG. 7C. Branch conduit may then be sewn, sintered or otherwise attached to body region 43 at depression 39.

Figure 9A:
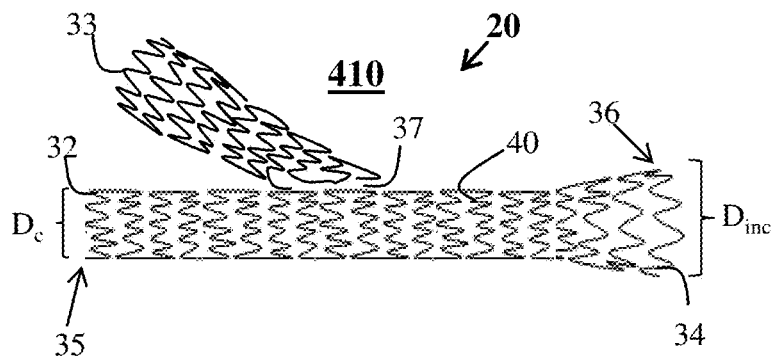
FIG. 9A is a side view of an embodiment of a support structure of the vascular graft similar to the embodiment shown in FIG. 1B, illustrating the support structure prior to combination with the biocompatible layer, according to one aspect of the present invention.
Figure 9B:
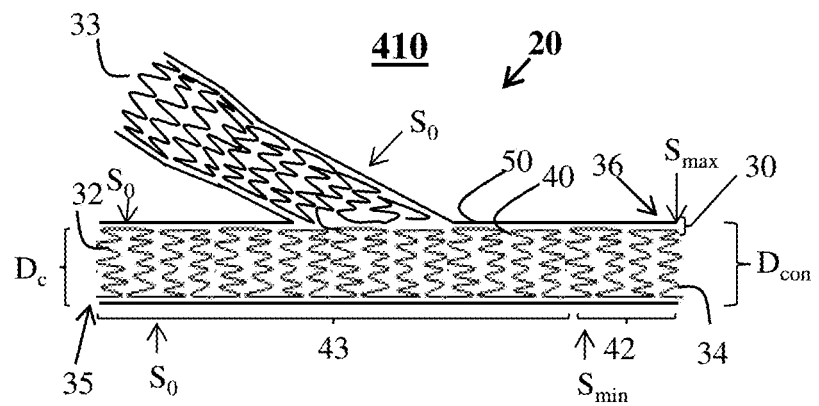
FIG. 9B is a schematic view of an embodiment of the vascular graft shown in FIG. 1B after combining the support structure shown in FIG. 9A with the biocompatible layer, according to one aspect of the present invention.
Figure 9C:
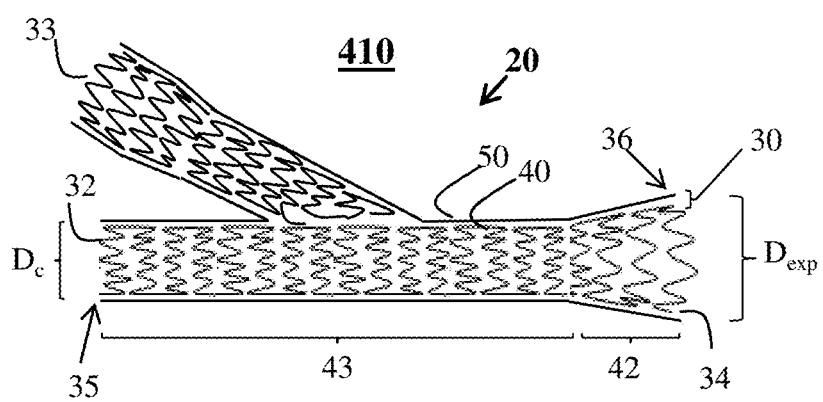
FIG. 9C is a schematic view of an embodiment similar to the vascular graft shown in FIG. 1B after expanding the outflow region of the support structure of the vascular graft shown in FIG. 9B, according to one aspect of the present invention.

Turning now to FIGS. 9A-9H, there is shown various views of another embodiment of the bifurcated vascular graft 410 similar to that shown in FIGS. 1B, 6A-6C and having a branch conduit 99 with a pre-fabricated and pre-expanded flared configuration at second inflow aperture 33 of the branch conduit 99 prior to implantation. With the exception of this flared configuration, the vascular graft 410 may have the same structure, components and configuration as that of the vascular graft 110 of FIGS. 1B and 6A-6C. This pre-fabricated, pre-expanded flared configuration anchors and provides rigidity and structure to the adjoining conduit body 43. The flared end may also facilitate vascular attachment and implantation. FIG. 9A shows a side view of an embodiment of a support structure 40 of the bifurcated vascular graft 110 shown in FIGS. 1B, 6A-6C, illustrating the support structure 40 prior to combination with the biocompatible layer 50 to form wall 30. FIG. 9B shows a schematic view of an embodiment of the bifurcated vascular graft 110 shown in FIG. 1B, 6A-6C after combining the support structure 40 shown in FIG. 9A with the biocompatible layer 50 to form wall 30. FIG. 9C shows a schematic view of an embodiment of the bifurcated vascular graft 410 construction shown in FIGS. 1B and 6A-6C after expanding the outflow end 36 of the support structure 40 of the bifurcated vascular graft 410 shown in FIG. 9B. FIG. 9D is a photograph showing a working prototype of the embodiment of the support structure 40 shown in FIG. 9A. FIG. 9E is a photograph of a working prototype of the embodiment of the bifurcated vascular graft shown in FIG. 9B, depicting the constrained effective outer diameter measurement $D_{con}$ of the support structure 40 along the outflow region 42. FIG. 9F is a photograph of a working prototype of the embodiment of the bifurcated vascular graft shown in FIG. 9C, depicting the expanded effective outer diameter measurement $D_{exp}$ of the support structure 40 along the outflow region 42 and an expanded effective outer diameter measurement $D_{exp}$ along an inflow region 44 proximal to the second inflow aperture 33. FIG. 9G is another photograph similar to FIG. 9F further illustrating a border 94 which is used in FIG. 9H to show schematically as a detail view of a representative cross-section of an embodiment of FIGS. 9B and 9C.

Referring to FIG. 9G, an extension conduit 51 is shown assembled to a flared socket-like construction. Utilizing the flared second inflow aperture 33, the extension conduit can connect to the luminal surface of branch conduit 99 when the branch conduit is covered with the biocompatible layer on one or both of the interior and exterior surfaces of the branch's support structure. When an extension conduit comprising a thicker wall 89 than the wall thicknesses 87 and 88 of the inner biocompatible layer 55 and outer compatible layer 54 respectively, the enlargened inner diameter of the branch provides sufficient room for the extension conduit to have a diameter that is substantially the same as the inner diameter of all or at least a majority of the branch conduit's inner luminal diameter.

Those skilled in the art will appreciate that in the example embodiments shown in FIGS. 9A-9G, the bifurcated vascular graft 110 and various features of the support structure 40 function in substantially the same way as described in the relevant paragraphs above.

In accordance with one example embodiment, a vascular graft 110 comprises: a conduit 20 having a wall 30, the conduit 20 comprising: at least one inflow aperture 32 at an inflow end 35 at a body region 43; and an outflow aperture 34 at an outflow end 36 at an outflow region 42 opposite from the at least one inflow aperture 32; wherein the wall 30 comprises a support structure 40 and a biocompatible layer 50; wherein prior to combination with the biocompatible layer 50 to form the wall 30, the support structure 40 comprises multiple effective outer diameter measurements along its length comprising a constant effective outer diameter measurement $D_c$ along the body region, and an effective outer diameter measurement $D_{inc}$ along the outflow region that is incrementally greater at each segment along the support structure 40 that is incrementally more distal from the at least one inflow aperture 32; wherein after combination with the biocompatible layer 50 to form the wall 30, the support structure 40 in the outflow region 42 is under continuous compressive stress S resulting from a continuous applied load caused by the biocompatible layer which maintains the support structure 40 in the outflow region at a constrained effective outer diameter measurement $D_{con}$ that is not incrementally greater at each segment along the support structure that is incrementally more distal from the at least one inflow aperture; and wherein after application of a counter force to the support structure 40 in the outflow region 42 the outflow region 42 is reconfigured from the constrained effective outer diameter measurement $D_{con}$ to an expanded effective outer diameter measurement $D_{exp}$, at least a portion of which is at least one millimeter greater than the constrained effective outer diameter measurement $D_{con}$.

The straight and bifurcated or T-shaped vascular grafts (e.g., the grafts 10 and 110) of the present invention can be used for a variety of applications, including, for example, for replacement or bypass of diseased vessels in patients suffering from occlusive or aneurysmal diseases, in trauma patients requiring vascular replacement, for dialysis access, to improve flow dynamics and reduce arterialized pressure during surgical anastomosis, or other vascular procedures routinely performed by a medical practitioner, as will be apparent to those skilled in the art.

In operation, the present taught vascular grafts (e.g., the grafts 10 and 110) are deployed for implantation into a body passage (e.g., a blood vessel). Embodiments of the present invention contemplate any operable method of deploying a vascular graft 10/110 for implantation into a body passage safely and effectively. Suitable methods will be apparent to the skilled medical practitioner. For example, one known method of deploying such a graft is to use a sheath with a tear line or "rip cord". The graft is contained within one or more sheaths for delivery to the desired location, preferably in a compressed condition such that the outer diameter of the sheath(s) is 2 or more millimeters smaller than the vessel the graft (or graft portion) is intended to be implanted within. Once properly located, a cord is pulled to separate the sheath along a tear line, and the sheath is then unwrapped from the graft and removed, leaving the graft in place at least partially due to the graft's self-expanding qualities. The general method of installing a graft using a single sheath in this manner is well known in the art, and as such requires no further description.

Once implanted in a body passage, the outflow region 42 of the vascular graft 10 can be expanded to maintain or restore patency of the graft, even after extensive duration of time passing from the time of original implantation (e.g., weeks, months, years). For example, if a portion of the graft collapses (e.g., due to tissue in-growth and eventually thrombosis formation), becomes stenosed, or sustains intimal hyperplasia, patency can be restored by expanding the outflow region 42 of the vascular graft 10 according to inventive methods described herein.

Figure 10A:
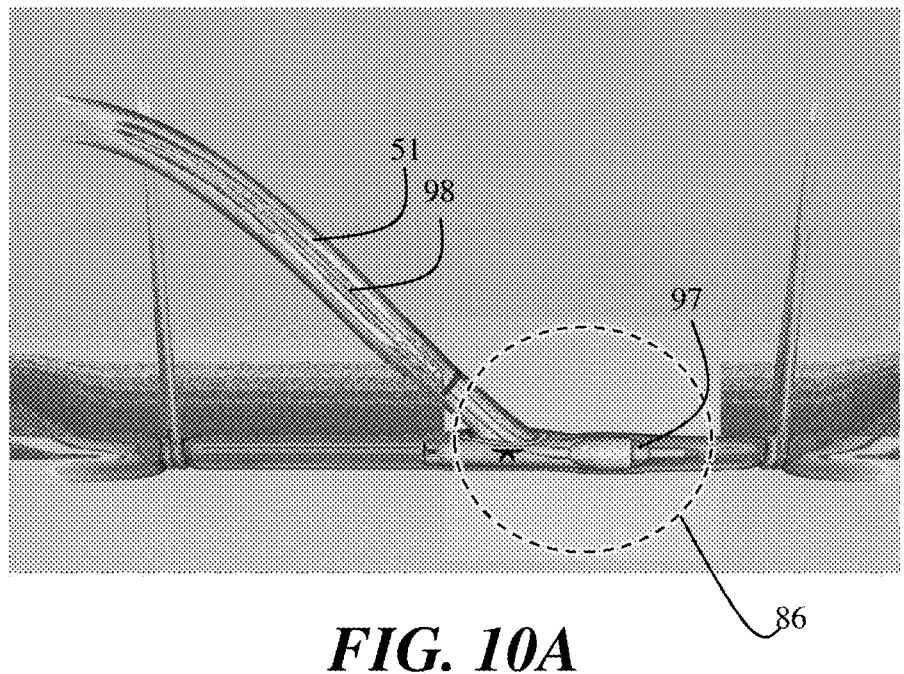
FIG. 10A is a schematic illustration of an expandable device similar to the embodiment of FIG. 9F, being used to expand the outflow region of a vascular graft, according to one aspect of the present invention.
Figure 10B:
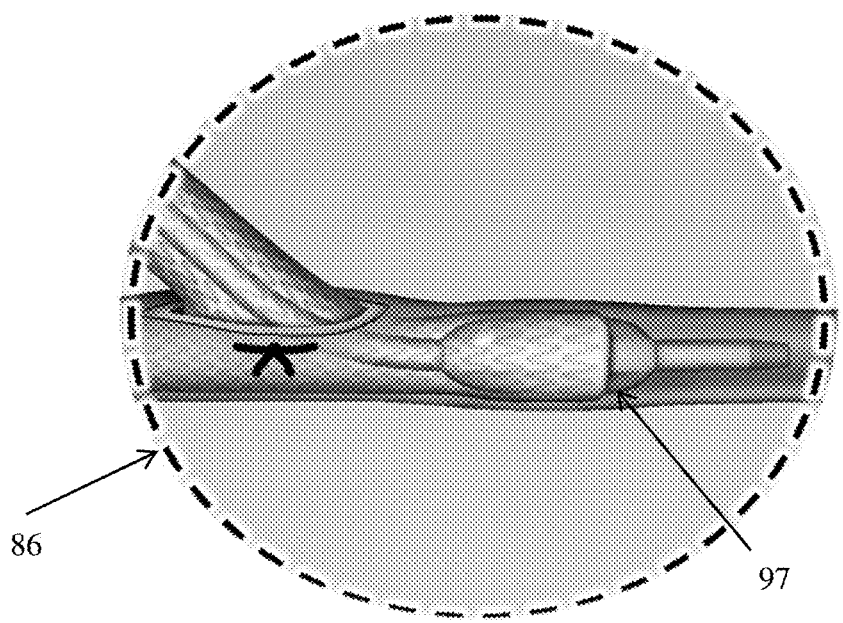
FIG. 10B is a detail view taken about border 86 of FIG. 10B, according to one aspect of the present invention.

FIGS. 10A and 10B are schematic illustrations of an expandable device being used to expand the outflow region 42 of an embodiment of vascular graft 10 which is provided with a bifurcated construction, although may also be employed for non-bifurcated constructions. More specifically, FIG. 10B is a detail view taken about the border 86 of FIG. 10A. In the example shown in FIGS. 10A-10B, the expandable device comprises a balloon catheter 98 with a balloon 97. Those skilled in the art, however, will appreciate that any expandable device which is capable of applying a counter force comprising a radial expansion force can be used. FIGS. 10A-10B are also instructive as to the installation of the graft 110 illustrated in this embodiment.

Figure 11:
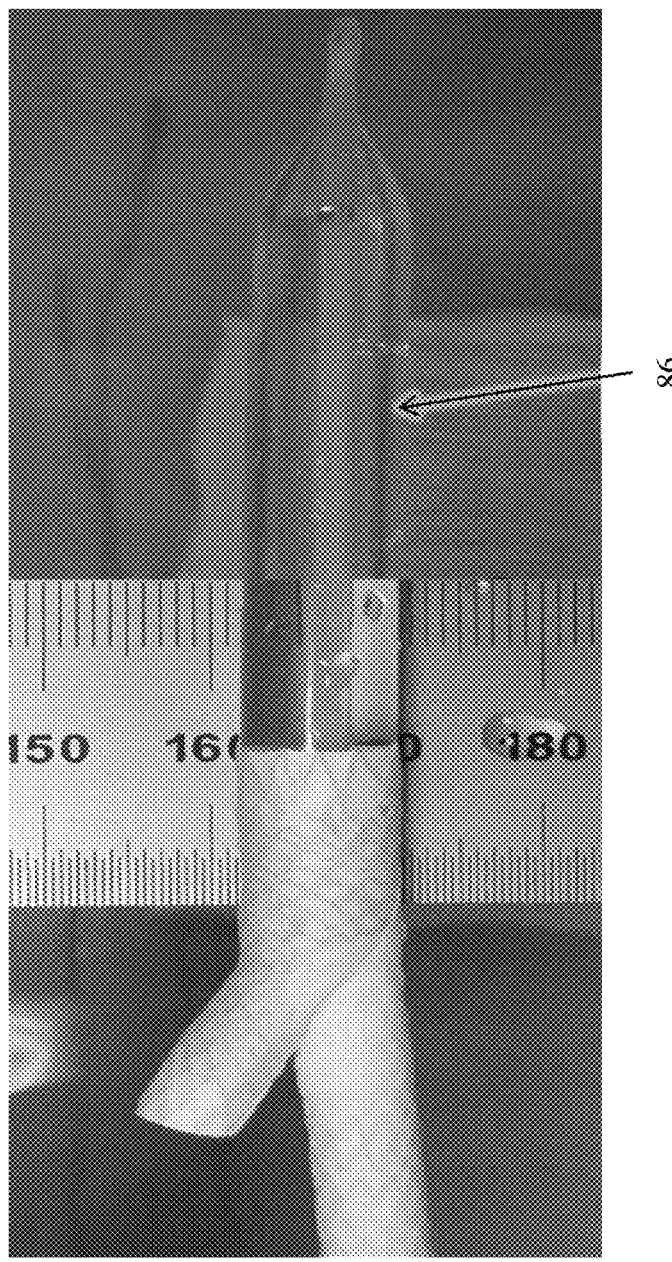
FIG. 11 is a photograph demonstrating an expandable device being used to expand the outflow region of a vascular graft, according to one aspect of the present invention.

FIG. 11 is a photograph demonstrating an expandable device 86 being used to expand an outflow region 42 of a vascular graft 110 which is provided with a bifurcated construction. The expandable device would be equally applicable to straight vascular grafts such as vascular graft 10.

Those skilled in the art will readily envision a variety of methods for expanding an outflow region 42 of the vascular graft 10.

In accordance with an example embodiment, a method 100 of expanding an outflow region 42 of an implanted vascular graft 10 generally comprises the steps of (a) identifying or providing 102 a vascular graft 10 having a support structure configured with a flared outflow region 42 according to any aspect of the present invention; and (b) applying a counter force 108 to the support structure 40 in the flared outflow region 42 to expand the outflow region 42.

In step 102, the implanted vascular graft 10 comprises: a conduit 20 having a wall 30, the conduit 20 comprising: at least one inflow aperture 32 at an inflow end 35 of a body region 43; and an outflow aperture at the outflow end of an outflow region 42 opposite from the at least one inflow aperture 32; wherein the wall comprises a support structure 40 and a biocompatible layer 50; wherein the support structure 40 in the outflow region 42 is under compressive stress S resulting from an applied load caused by the biocompatible layer 50. In step 108, applying a counter force to the support structure 40 in the outflow region 42 reconfigures the support structure 40 in the outflow region 42 from a constrained effective outer diameter measurement $D_{con}$ to an expanded effective outer diameter measurement $D_{exp}$ that is greater than the constrained effective outer diameter measurement $D_{con}$, thereby expanding the outflow region 42 of the implanted vascular graft 10.

Figure 12:
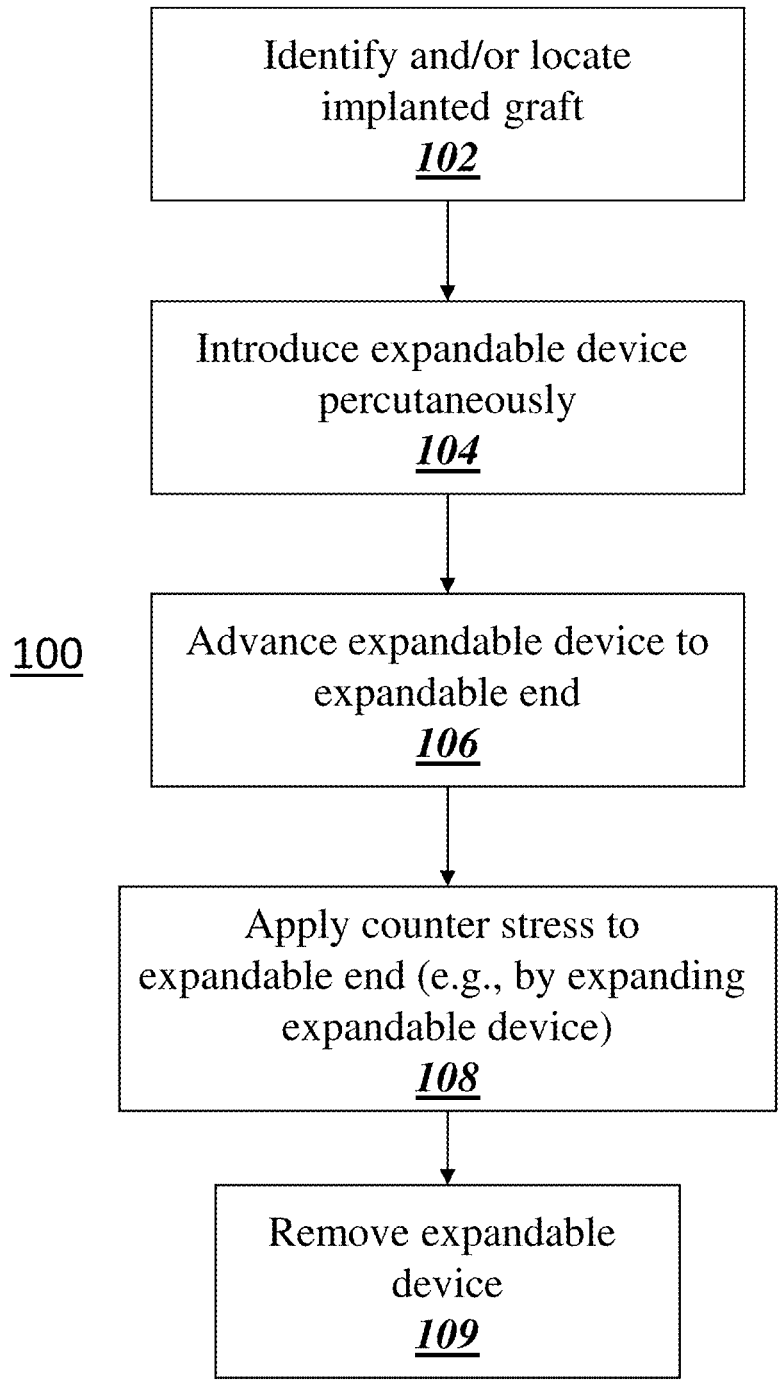
FIG. 12 is a flow chart depicting a method of expanding an outflow region of a vascular graft according to one aspect of the present invention.

FIG. 12 shows a flow chart depicting an exemplary embodiment of a method 100 of expanding an outflow region 42 of a vascular graft 10 according to one aspect of the present invention.

As shown in the exemplary embodiment in FIG. 12, a method of expanding an outflow region 42 of an implanted vascular graft 10 includes steps 102 to 108. Step 102 comprises: (a) identifying an implanted vascular graft 10 described herein. To expand the implanted vascular graft 10 identified in step 102, step 108 is conducted. Step 108 comprises: (b) applying a counter force to the support structure 40 in the outflow region 42 in accordance with the detailed description herein, thereby expanding the outflow region 42 of the implanted vascular graft 10.

It should be appreciated that although the expandable outflow region 42 can be expanded at any time post-implantation, in practice the outflow region is advantageously expanded when the outflow region 42 has collapsed or stenosed or has sustained intimal hyperplasia. In such instances, the outflow region 42 that has collapsed, stenosed, or sustained intimal hyperplasia impairs patency of a vessel in which the implanted vascular graft 10 is implanted.

In an exemplary embodiment, applying the counter force comprises expanding an expandable device in the outflow region 42 of the implanted vascular graft 10. In an exemplary embodiment, prior to expanding the expandable device (step 108) the expandable device is advanced to the outflow end (step 106).

In an exemplary embodiment, prior to advancing the expandable device to the outflow region (step 106), the expandable device is introduced into the implanted graft percutaneously (step 104). In an exemplary embodiment, after expanding the expandable device 10, the expandable device is removed according to step 110.

In an exemplary embodiment, the expanded effective outer diameter measurement $D_{exp}$ is at least one millimeter greater than the constrained effective outer diameter measurement $D_{con}$. In another exemplary embodiment, the expanded effective outer diameter measurement $D_{exp}$ is at least one millimeter greater than the constrained effective outer diameter measurement $D_{con}$ along any portion of the support structure 40 in the outflow region 42.

Contemplated herein are various methods for making a vascular graft 10 disclosed herein.

Figure 13:
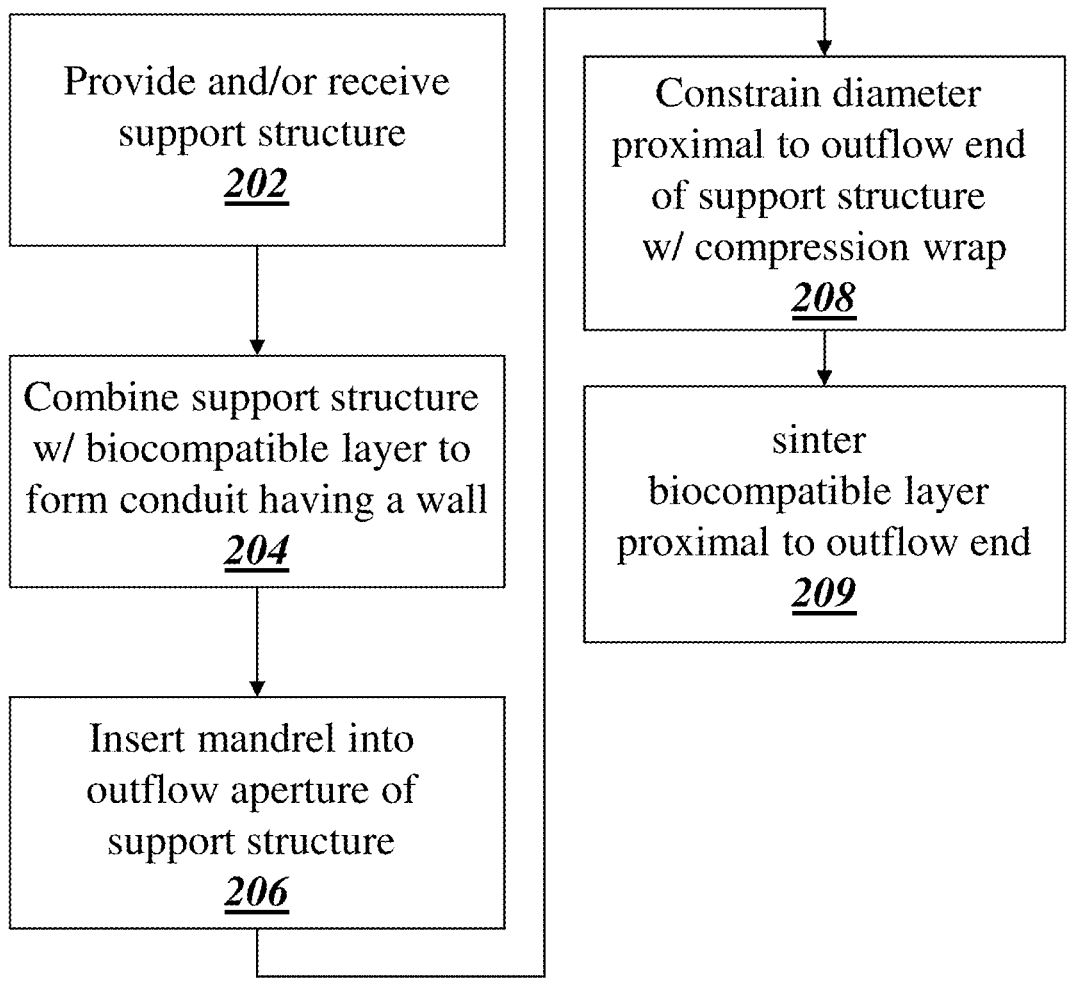
FIG. 13 is a flow chart depicting a method of making a vascular graft according to one aspect of the present invention.

FIG. 13 is a flow chart depicting an exemplary method 200 of making a vascular graft 10 according to one aspect of the present invention.

In an exemplary embodiment, a method 200 of making a vascular graft 10 having an expandable outflow region comprises steps 202 to 209. In the example shown in FIG. 13, the method 200 proceeds with: (a) providing a support structure (step 202) in accordance with the detailed description provided herein. comprising at least one inflow aperture 32 at an inflow end 35 of a body region 43 and an outflow aperture 34 at an outflow end 36 of an outflow region 42 opposite from the at least one inflow aperture 32. The support structure 40 may be sized through the use of various mandrels to have multiple effective outer diameter measurements comprising a constant effective outer diameter measurement $D_c$ along the body region 43 of the support structure 40 in addition to an incrementally increasing effective outer diameter measurement $D_{inc}$ along the outflow region 42 of the support structure. It should be appreciated by those skilled in the art that the support structure 40 provided in step 202 can include any support structure 40 contemplated herein, including the embodiments shown in FIGS. 2A, 5A, 7A, and 8A, which can be provided with an inflow region 44 or outflow region 42 with a flared configuration illustrated in FIGS. 3A-3O, or any combination thereof.

Once the support structure 40 is provided in step 202, the method 200 proceeds with step 204 which comprises: (b) combining the support structure 40 with at least one biocompatible layer 50 to form a conduit 20 having a wall 30 comprising the support structure 40 and the at least one biocompatible layer 50.

After combining the support structure 40 with the biocompatible layer 50 in step 204, the method continues with step 206 which comprises: (c) inserting a mandrel into the outflow aperture 34 proximal to the outflow end 36 of the support structure 40.

With the mandrel inserted into the outflow aperture 34, the method proceeds with step 208, which comprises: (d) constraining the incrementally increasing effective outer diameter measurement $D_{inc}$ along the outflow region 42 of the support structure 40, for example with a compression wrap, in such a way that a continuous compressive stress S results from a continuous applied load caused by the biocompatible layer 50 which maintains the support structure 40 along the outflow region 42 in a constrained effective outer diameter measurement $D_{con}$ that is generally uniform with the constant effective outer diameter measurement $D_c$.

To conform the biocompatible layer 50 to the support structure 40, the method comprises step 209 of (e) sintering the biocompatible layer 50 at a segment in the outflow region 42.

FIG. 14A is a photograph illustrating step 206 of a method 200 of making a vascular graft 10 according to one aspect of the present invention in which a mandrel is inserted into the outflow end 36 of the vascular graft 10 prior to constraining the effective outer diameter measurement along the outflow end of the support structure 40 with a compression wrap.

FIG. 14B is a photograph illustrating a step 206 of a method 200 of making a vascular graft 10 according to one aspect of the present invention in which a compression wrap is used to constrain the effective outer diameter measurement along the outflow end of the support structure 40.

In another exemplary embodiment of the invention, a vascular graft 510 is illustrated in FIGS. 15A-C. The graft 510 is formed by a pair of bifurcated graft subassemblies 302a and 302b (collectively, the "bifurcated subassemblies 302"), arranged as mirror images of each other, and connected by an extension conduit 51. Each of the bifurcated subassemblies 302, may be arranged, as illustrated, to resemble the bifurcated vascular grafts 110. As discussed in more detail with respect to FIGS. 16A-16C and 17A-17C, further vascular graft embodiments can be formed by exchanging one or both of the bifurcated subassemblies 302 with graft subassemblies resembling the graft 10. Accordingly, the components of the graft 510 that are akin to those of the grafts 10 and/or 110 (e.g., the conduit 20, the wall 30, the support structure 40, the biocompatible layer 50, etc.), have correspondingly been given the same reference numerals as those used with respect to the above discussion of the grafts 10 and 110.

FIG. 15A illustrates the bifurcated subassemblies without a biocompatible layer 50, while FIG. 15B illustrates the bifurcated subassemblies with both the biocompatible layer 50 and an extension lumen 51 establishing a continuous conduit between the subassemblies. In various embodiments, the extension lumen 51 may be a multilayer laminate configuration of ePTFB and has a thickness 89 greater than the thickness of the inner layer 55 and outer layer 54 of biocompatible layer 50.

As illustrated in FIG. 15C, the bifurcated subassemblies 302a and 302b are insertable within a first vessel portion 306a and a second vessel portion 306b, respectively (collectively the vessel portions 306). The conduit section 51 is arranged as a luminal structure that provides fluid communication, e.g., blood flow, between the bifurcated subassemblies 302, and therefore, the vessel portions 306. Due to the bifurcations of both of the subassemblies 302, at least a portion of blood flow, i.e., the blood flow that is not diverted into the conduit section 51, may also continue through and past the subassemblies 302. The wall 30 of the conduit section 51 may be unreinforced, that is, including only the biocompatible layer 50 and not the support structure 40. It is to be appreciated that the conduit section 51 may be any desired length. For example, relatively shorter lengths may be used in some embodiments, e.g., to bridge or bypass an occlusion in a blood vessel, while relatively longer lengths are used in other embodiments, e.g., to connect an artery to a vein for assisting in dialysis. In one embodiment, the conduit section 51 is between about 20 mm and 150 mm, although other lengths are also possible.

It is to be appreciated that the graft 510 may be used in embodiments in which the vessels 306 are different parts of the same vessel, or in embodiments in which the vessel portions 306 are parts of different vessels. For example, if the vessel portions 306 are part of the same vessel, the graft 510 may be used to create a bypass of a section of the vessel located between the vessel portions 306a and 306b. For example, an occlusion, such as plaque buildup, may completely or partially impede or block blood flow within a blood vessel of a patient. In this example, the graft 510 may accordingly be installed such that the conduit section 51 provides a bypass of the occlusion when the subassemblies 302 are installed into the blood vessel on opposite sides of the occlusion.

As another example, in one embodiment, one of the vessel portions 306 (e.g., the vessel 306a) is a part of an artery, and the other of the vessel portions (e.g., the vessel 306b) is part of a vein. In this way, the conduit section 51 diverts a portion of blood flowing through the artery into the vein. For example, this embodiment may be particularly useful in that the conduit section 51 may provide a suitable target to assist a patient in undergoing dialysis, e.g., with the blood diverted between the artery and vein taken from and re-injected into the conduit section 51, thus avoiding unnecessary damage to a patient's vasculature that may result from repeated dialysis treatments. In such embodiments, the ability for the conduit section 51 to seal after needle punctures is enhanced versus the properties of the vascular graft 510 that might be covered by a thinner material than used in the conduit section 51.

Figure 16A:
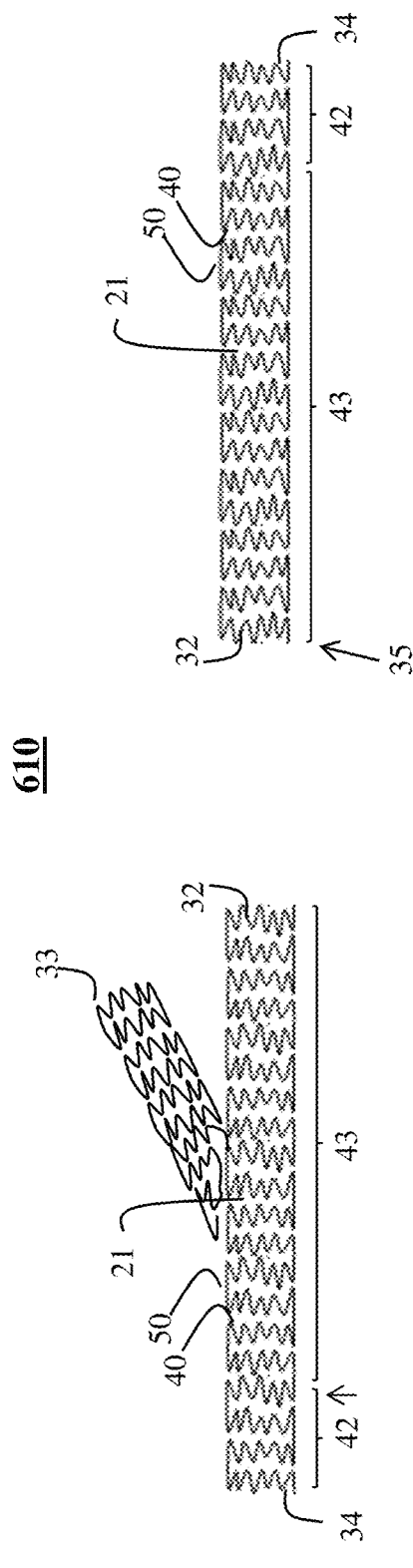
FIG. 16A is a schematic view of a vascular graft according to another embodiment of the present invention illustrating the support structure prior to combination with a biocompatible layer, according to one aspect of the present invention.
Figure 16B:
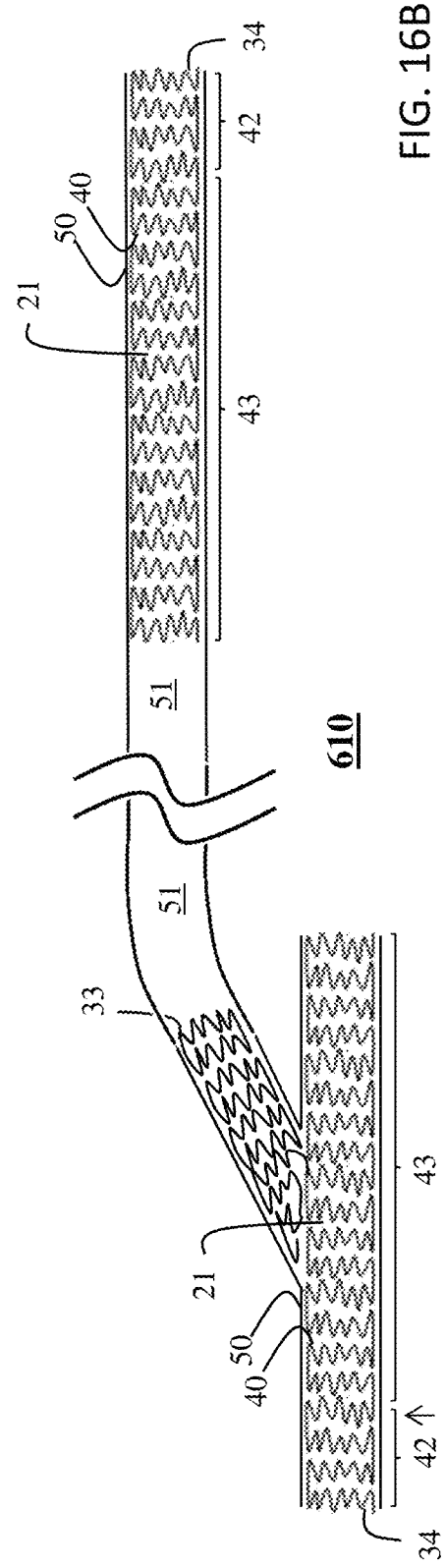
FIG. 16B is a schematic view of an embodiment of the support structure of FIG. 16A after the biocompatible layer(s) has been added to the support structure, according to one aspect of the present invention.

A vascular graft 610 is illustrated in FIGS. 16A-16C, and generally resembles the graft 510, e.g., including a pair of graft subassemblies 312a and 312b (collectively, the "subassemblies 312") connected together by a conduit section 51. Unlike the graft 510, in which both of the subassemblies 302 resemble the bifurcated graft 110 of FIG. 1B, the subassembly 312b of the graft 610 is a straight graft subassembly that generally resembles the straight vascular graft 10 of FIG. 1A, while the subassembly 312a is a bifurcated graft subassembly resembling the graft 110. It is noted that due to the lack of bifurcation of the subassembly 312b in this embodiment, blood flowing through the vessel portion 306b may be blocked or impeded by the subassembly 312b. That is, all or most of the blood flow that is flowing through the vessel portion 306b in the direction of the subassembly 312a from the subassembly 312b will be diverted through the conduit section 51 instead of continuing through the vessel portion 306b. Thus, the graft 610 is particularly advantageous in embodiments in which blood flow through the vessel portion 306b on both sides of the subassembly 312b is not necessary, e.g., such as when the vessel portions 306 are part of the same vessel, and an occlusion is present therebetween, and thus a bypass of that occlusion is desired.

A vascular graft 710 is illustrated in FIGS. 17A-17C, and generally resembles the grafts 510 and/or 610, e.g., including a pair of graft subassemblies 322a and 322b (collectively, the "subassemblies 322") connected together by a conduit section 51. Similar to the subassembly 312b of the graft 610, both of the subassemblies 322 are straight graft subassemblies, resembling the graft 10 without bifurcations. For this reason, and similar to the subassembly 312b, both of the subassemblies 322 may block or impede blood flow through the respective vessel portion 306 in which they are inserted. Thus, the graft 710 may accordingly be particularly useful in embodiments in which an occlusion is present between the vessel portions 306, and thus a bypass of that occlusion is desired.

It is to be appreciated that the subassemblies 510, 610, and 710 may include tapered, trumpeted, or flared inflow and/or outflow regions, according to the above descriptions thereof. That is, the support structures 40 in the subassemblies 510, 610, and/or 710 may be arranged and constructed of nitinol or other shape memory material, or otherwise be configured to naturally transition to a radially expanded shape. Additionally, the support structure 40 may, similar to the above disclosure herein, be further radially expanded by use of an inflatable balloon 97 or other device inserted within the support structure 40.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the present invention, and exclusive use of all modifications that come within the scope of the appended claims is reserved. Within this specification embodiments have been described in a way which enables a clear and concise specification to be written, but it is intended and will be appreciated that embodiments may be variously combined or separated without parting from the invention. It is intended that the present invention be limited only to the extent required by the appended claims and the applicable rules of law.

It is also to be understood that the following claims are to cover all generic and specific features of the invention described herein, and all statements of the scope of the invention which, as a matter of language, might be said to fall therebetween.

What is claimed is:

1. A graft comprising a support structure having an expandable outflow region, and a biocompatible layer configurable from a first shape to a second shape, the second shape being a flared shape having an expanded diameter along at least a portion of a length of the expandable outflow region, and the first shape having a constrained diameter, smaller than the expanded diameter, due to the biocompatible layer constraining the support structure along the expandable outflow region under a continuous radial inward compressive stress;

wherein the support structure assumes the flared shape prior to combination with the biocompatible layer to form a wall, and the flared shape has multiple effective outer diameter measurements, and the support structure assumes the first shape after combination with the biocompatible layer to form the wall, and the constrained diameter of the first shape is a generally uniform effective outer diameter.

2. The graft of claim 1, wherein the support structure has a body region, and when the support structure is in the first shape, the continuous radial inward compressive stress applied by the biocompatible layer in the expandable outflow region is greater than a compressive stress applied by the biocompatible layer in the body region.

3. The graft of claim 1, wherein the continuous radial inward compressive stress applied by the biocompatible layer in the expandable outflow region when the support structure is in the first shape causes an elastic deformation of the support structure in the expandable outflow region.

4. The graft of claim 1, wherein the multiple effective outer diameter measurements comprise an effective outer diameter measurement that is incrementally greater at each segment along the outflow region of the support structure.

5. The graft of claim 4, wherein the support structure has a body region, and when the support structure is in the first shape, the generally uniform effective outer diameter of the support structure along the outflow region is approximately equal to a constant effective outer diameter of the support structure along the body region.

6. The graft of claim 5, wherein a counter force comprising a radial expansion force applied to the support structure in the outflow region reconfigures the support structure along the outflow region from the constrained diameter to the expanded diameter along at least a portion of the outflow region of the support structure.

7. The graft of claim 1, wherein the support structure is constructed of a shape memory alloy.

8. The graft of claim 7, wherein the shape memory alloy includes at least one of aluminum, cobalt, chromium, copper, gold, iron, nickel, platinum, tantalum or titanium.

9. The graft of claim 1, wherein the support structure is constructed of nitinol.

10. The graft of claim 1, wherein the biocompatible layer comprises an expandable polymer.

11. The graft of claim 1, wherein the biocompatible layer comprises ePTFE.

12. The graft of claim 1, wherein the support structure comprises a zigzag wire shape.

13. The graft of claim 1, wherein the biocompatible layer encapsulates the support structure.

* * * * *